(12) United States Patent
Pajouhesh et al.

(10) Patent No.: US 7,511,077 B2
(45) Date of Patent: Mar. 31, 2009

(54) DIAMINE CALCIUM CHANNEL BLOCKERS

(75) Inventors: Hassan Pajouhesh, Vancouver (CA);
Hossein Pajouhesh, Coquitlam (CA);
Yanbing Ding, Richmond (CA);
Terrance P. Snutch, Vancouver (CA);
Francesco Belardetti, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 198 days.

(21) Appl. No.: 11/351,224

(22) Filed: Feb. 8, 2006

(65) Prior Publication Data

US 2006/0235050 A1    Oct. 19, 2006

Related U.S. Application Data

(60) Provisional application No. 60/656,554, filed on Feb. 24, 2005, provisional application No. 60/651,829, filed on Feb. 9, 2005.

(51) Int. Cl.
C07C 211/09 (2006.01)
C07C 233/30 (2006.01)
A61K 31/165 (2006.01)

(52) U.S. Cl. ............... 514/617; 514/616; 564/152; 564/161

(58) Field of Classification Search .......... None
See application file for complete search history.

(56) References Cited

U.S. PATENT DOCUMENTS

| | | | |
|---|---|---|---|
| 2,951,092 A * | 8/1960 | Sowinski et al. ............ 564/47 |
| 3,876,702 A | 4/1975 | Petersen et al. |
| 4,467,094 A * | 8/1984 | Casagrande et al. ......... 546/334 |
| 4,988,735 A * | 1/1991 | Casagrande et al. ......... 514/648 |
| 5,324,728 A * | 6/1994 | Sekine et al. ............ 514/253.01 |
| 5,428,038 A | 6/1995 | Chatterjee et al. |
| 5,646,149 A | 7/1997 | Hellberg et al. |
| 5,703,071 A | 12/1997 | Itoh et al. |
| 6,011,035 A | 1/2000 | Snutch et al. |
| 6,294,533 B1 | 9/2001 | Snutch et al. |
| 6,310,059 B1 | 10/2001 | Snutch |
| 6,458,781 B1 | 10/2002 | Connor et al. |
| 6,492,375 B2 | 12/2002 | Snutch |
| 6,943,168 B2 | 9/2005 | Snutch et al. |
| 6,949,554 B2 | 9/2005 | Snutch et al. |
| 6,951,862 B2 | 10/2005 | Snutch et al. |
| 2002/0019389 A1 | 2/2002 | Kim |
| 2004/0044004 A1 | 3/2004 | Snutch et al. |
| 2004/0147529 A1 | 7/2004 | Snutch et al. |
| 2004/0192703 A1 | 9/2004 | Snutch et al. |
| 2004/0259866 A1 | 12/2004 | Snutch et al. |
| 2004/0266784 A1 | 12/2004 | Snutch et al. |

FOREIGN PATENT DOCUMENTS

| DE | 2320058 | 11/1973 |
|---|---|---|
| GB | 873691 | 7/1961 |
| WO | WO-00/01375 | 1/2000 |
| WO | WO-01/45709 | 6/2001 |
| WO | WO-01/46166 | 6/2001 |
| WO | WO-01/49670 | 7/2001 |
| WO | WO-2004/089377 | 10/2004 |
| WO | WO-2004/089922 | 10/2004 |

OTHER PUBLICATIONS

Stelakatos et al, Journal of the Chemical Society, Section C Organic, 1966, vol. 13, pp. 1191-1199.*
Augustine et al., Annu. Rev. Neurosci. (1987) 10:633-693.
Backonja et al., JAMA (1998) 280:1831-1836.
Bowersox et al., J. Pharmacol. Exp. Ther. (1996) 279:1243-1249.
Caraceni et al., J. Pain & Symp. Manag. (1999) 17:441-445.
Catterall, Annu. Rev. Cell Dev. Biol. (2000) 16:521-555.
Cesena, Neuro. Sci. Lett. (1999) 262:101-104.
Cheng et al., Anesthesiology (2000) 92:1126-1131.
Di Trapani et al., Clin. Ter. (2000) 151:145-148.
Dogrul et al., Pain (2003) 105:159-168.
Dooley, Current Opinion in CPNS Investigational Drugs (1999) 1:116-125.
Field et al., Pain (1999) 80:391-398.
Gomora et al., Mol. Pharmacol. (2001) 60:1121-1132.
Gould et al., PNAS USA (1983) 80:5122-5125.
Grantham et al., Brit. J. Pharmacol. (1944) 111:483-488.
Hatakeyama et al., Neuro Report (2001) 12:2423-2427.
Heading, Curr. Opin. CPNS Investigational Drugs (1999) 1:153-166.
Heady et al., Jpn. J. Pharmacol. (2001) 85:339-350.
Houtchens et al., Multiple Sclerosis (1997) 3:250-253.
Huguenard, Annu. Rev. Physiol. (1996) 58:329-348.
Ino et al., PNAS USA (2001) 98:5323-5328.
Kim et al., Mol. Cell Neurosci. (2001) 18:235-245.
King et al., J. Biol. Chem. (1989) 264:5633-5641.
Laird et al., Annal. Pharmacotherap. (2000) 34:802-807.
Magnus, Epilepsia (1999) 40:S66-S72.
Malmberg et al., J. Neurosci. (1994) 14:4882-4890.
Mathur, Seminars in Anesthesia, Perioperative Medicine and Pain (2000) 19:67-75.
Miller, Science (1987) 235:46-52.
Nicholson, Acta. Neurol. Scand. (2000) 101:359-371.
Ridgeway et al., Pain (2000) 85:287-289.
Rowbotham et al., JAMA (1998) 280:1837-1842.
Saegusa et al., PNAS USA (2001) 97:6132-6137.
Sluka, J. Pharmacol. Exp. Ther. (1998) 287:232-237.
Stea et al., PNAS USA (1994) 91:10576-10580.

(Continued)

Primary Examiner—Zinna N Davis
(74) Attorney, Agent, or Firm—Morrison & Foerster LLP

(57) ABSTRACT

Aromatic derivatives of aliphatic diamines are effective in ameliorating conditions characterized by unwanted calcium ion channel activity, especially T-type and N-type channels. These conditions include, for example, stroke and pain.

18 Claims, No Drawings

OTHER PUBLICATIONS

Su et al., J. Neurosci. (2002) 22:3645-3655.
Taylor et al., Epilepsy Res. (1998) 29:233-249.
Vanegas et al., Pain (2000) 85:9-18.
Wang et al., Soc. Neurosci. Abstr. (1998) 24:1626.
Castelnovo, Journal of Chromatography (1996) 676:77-85.
Harmat et al., Journal of Molecular Biology (2000) 297:747-755.
International Search Report for PCT/CA2006/000193, mailed on May 11, 2006, 9 pages.
Korbonits et al., Acta Chimica Acadamiae Scientiarum Hungaricae (1974) 82(2):231-234.
Lee et al., Journal of Combinatorial Chemistry (2003) 5:172-187.
Nakagawa et al., Japan J. Pharmacol. (1979) 29:271-283.
STN Columbus— Registry Database, Registry Nos. 548788-45-0, 548786-99-8, 548480-89-3, 548468-54-8, 548441-23-2, 547724-99-2, 547724-33-4 and 547711-13-7, no date provided.
Vertessy et al., Proteins: Structure, Function and Genetics (1997) 28:131-134.

* cited by examiner

DIAMINE CALCIUM CHANNEL BLOCKERS

RELATED APPLICATIONS

This application claims the benefit of U.S. Provisional Application No. 60/656,554, which was filed on Feb. 24, 2005, and U.S. Provisional Application No. 60/651,829, which was filed on Feb. 9, 2005. Those applications are incorporated herein by reference in their entirety.

TECHNICAL FIELD

The invention relates to compounds useful in treating conditions associated with calcium channel function. More specifically, the invention concerns compounds containing substituted or unsubstituted diamine derivatives of that are useful in treatment of conditions such as pain and other central nervous system diseases.

BACKGROUND ART

The entry of calcium into cells through voltage-gated calcium channels mediates a wide variety of cellular and physiological responses, including excitation-contraction coupling, hormone secretion and gene expression (Miller, R. J., Science (1987) 235:46-52; Augustine, G. J. et al., Annu Rev Neurosci (1987) 10: 633-693). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter and calcium channels, which also affects neurite outgrowth and growth cone migration in developing neurons.

Calcium channels mediate a variety of normal physiological functions, and are also implicated in a number of human disorders. Examples of calcium-mediated human disorders include but are not limited to congenital migraine, cerebellar ataxia, angina, epilepsy, hypertension, ischemia, and some arrhythmias. The clinical treatment of some of these disorders has been aided by the development of therapeutic calcium channel antagonists (e.g., dihydropyridines, phenylalkyl amines, and benzothiazapines all target L-type calcium channels) (Janis, R. J. & Triggle, D. J., In Calcium Channels: Their Properties, Functions, Regulation nad Clinical Relevance (1991) CRC Press, London).

Native calcium channels have been classified by their electrophysiological and pharmacological properties into T-, L-, N-, P/Q- and R-types (reviewed in Catterall, W., Annu Rev Cell Dev Biol (2000) 16: 521-555; Huguenard, J. R., Annu Rev Physiol (1996) 58: 329-348). T-type (or low voltage-activated) channels describe a broad class of molecules that transiently activate at negative potentials and are highly sensitive to changes in resting potential.

The L-, N- and P/Q-type channels activate at more positive potentials (high voltage-activated) and display diverse kinetics and voltage-dependent properties (Catterall (2000); Huguenard (1996)). L-type channels can be distinguished by their sensitivity to several classes of small organic molecules used therapeutically, including dihydropyridines (DHP's), phenylalkylamines and benzothiazepines. In contrast, N-type and P/Q-type channels are high affinity targets for certain peptide toxins produced by venomous spiders and marine snails: N-type channels are blocked by the ω-conopeptides ω-conotoxin GVIA (ω-CTx-GVIA) isolated from Conus geographus and ω-conotoxin MVIIA (ω-CTx-MVIIA) isolated from Conus magus, while P/Q-type channels are resistant to ω-CTx-MVIIA but are sensitive to the funnel web spider peptide, ω-agatoxin IVA (ω-Aga-IVA). R-type calcium channels are sensitive to block by the tarantula toxin, SNX-482.

Neuronal high voltage-activated calcium channels are composed of a large (>200 kDa) pore-forming $\alpha_1$ subunit that is the target of identified pharmacological agents, a cytoplasmically localized ~50-70 kDa β subunit that tightly binds the $\alpha_1$ subunit and modulates channel biophysical properties, and an ~170 kDa $\alpha_2\delta$ subunit (reviewed by Stea, et al., Proc Natl Acad Sci USA (1994) 91:10576-10580; Catterall (2000)). At the molecular level, nine different $\alpha_1$ subunit genes expressed in the nervous system have been identified and shown to encode all of the major classes of native calcium currents (Table 1).

TABLE 1

Classification of Neuronal Calcium Channels

| Native Class | cDNA | Gene Name | ω-AGA IVA | ω-CTx GVIA | ω-CTx MVIA | dihydro-pyridines |
|---|---|---|---|---|---|---|
| P/Q-type | $\alpha_{1A}$ | $Ca_V2.1$ | ✓ | — | — | — |
| N-type | $\alpha_{1B}$ | $Ca_V2.2$ | — | ✓ | ✓ | — |
| L-type | $\alpha_{1C}$ | $Ca_V1.2$ | — | — | — | ✓ |
| L-type | $\alpha_{1D}$ | $Ca_V1.3$ | — | — | — | ✓ |
| R-type | $\alpha_{1E}$ | $Ca_V2.3$ | — | — | — | — |
| L-type | $\alpha_{1F}$ | $Ca_V1.4$ | — | — | — | ✓ |
| T-type | $\alpha_{1G}$ | $Ca_V3.1$ | — | — | — | — |
| T-type | $\alpha_{1H}$ | $Ca_V3.2$ | — | — | — | — |
| T-type | $\alpha_{1I}$ | $Ca_V3.3$ | — | — | — | — |

Calcium channels have been shown to mediate the development and maintenance of the neuronal sensitization processes associated with neuropathic pain, and provide attractive targets for the development of analgesic drugs (reviewed in Vanegas, H. & Schaible, H-G., Pain (2000) 85: 9-18). All of the high-threshold Ca channel types are expressed in the spinal cord, and the contributions of L-, N and P/Q-types in acute nociception are currently being investigated. In contrast, examination of the functional roles of these channels in more chronic pain conditions strongly indicates a pathophysiological role for the N-type channel (reviewed in Vanegas & Schaible (2000) supra).

Mutations in calcium channel $\alpha_1$ subunit genes in animals can provide important clues to potential therapeutic targets for pain intervention. Genetically altered mice null for the $\alpha_{1B}$ N-type calcium channel gene have been reported by several independent groups (Ino, M. et al., Proc Natl Acad Sci USA (2001) 98(9): 5323-5328; Kim, C. et al., Mol Cell Neurosci (2001) 18(2): 235-245; Saegusa, H. et al., Proc Natl Acad Sci USA (2001) 97: 6132-6137; Hatakeyama, S. et al., Neuroreport (2001) 12(11): 2423-2427). The $\alpha_{1B}$ N-type null mice were viable, fertile and showed normal motor coordination. In one study, peripheral body temperature, blood pressure and heart rate in the N-type gene knock-out mice were all normal (Saegusa, et al. (2001)). In another study, the baroreflex mediated by the sympathetic nervous system was reduced after bilateral carotid occlusion (Ino, et al. (2001)). In another study, mice were examined for other behavioral changes and were found to be normal except for exhibiting significantly lower anxiety-related behaviors (Saegusa, et al. (2001)), suggesting the N-type channel may be a potential target for mood disorders as well as pain. In all studies, mice lacking functional N-type channels exhibit marked decreases in the chronic and inflammatory pain responses. In contrast, mice lacking N-type channels generally showed normal acute nociceptive responses.

Two examples of either FDA-approved or investigational drug that act on N-type channel are gabapentin and ziconotide. Gabapentin, 1-(aminomethyl)cyclohexaneacetic acid (Neurontin®), is an anticonvulsant originally found to be active in a number of animal seizure models (Taylor, C. P. et al., *Epilepsy Res* (1998) 29: 233-249). Subsequent work has demonstrated that gabapentin is also successful at preventing hyperalgesia in a number of different animal pain models, including chronic constriction injury (CCI), heat hyperalgesia, inflammation, diabetic neuropathy, static and dynamic mechanoallodynia associated with postoperative pain (Taylor, et al. (1998); Cesena, R. M. & Calcutt, N. A., *Neurosci Lett* (1999) 262: 101-104; Field, M. J. et al., *Pain* (1999) 80: 391-398; Cheng, J-K., et al., *Anesthesiology* (2000) 92: 1126-1131; Nicholson, B., *Acta Neurol Scand* (2000) 101: 359-371).

While its mechanism of action is not completely understood, current evidence suggests that gabapentin does not directly interact with GABA receptors in many neuronal systems, but rather modulates the activity of high threshold calcium channels. Gabapentin has been shown to bind to the calcium channel $\alpha_2\delta$ ancillary subunit, although it remains to be determined whether this interaction accounts for its therapeutic effects in neuropathic pain.

In humans, gabapentin exhibits clinically effective anti-hyperalgesic activity against a wide ranging of neuropathic pain conditions. Numerous open label case studies and three large double blind trials suggest gabapentin might be useful in the treatment of pain. Doses ranging from 300-2400 mg/day were studied in treating diabetic neuropathy (Backonja, M. et al., *JAMA* (1998) 280:1831-1836), postherpetic neuralgia (Rowbotham, M. et al., *JAMA* (1998) 280: 1837-1842), trigeminal neuralgia, migraine and pain associated with cancer and multiple sclerosis (Di Trapini, G. et al., *Clin Ter* (2000) 151: 145-148; Caraceni, A. et al., *J Pain & Symp Manag* (1999) 17: 441-445; Houtchens, M. K. et al., *Multiple Sclerosis* (1997) 3: 250-253; see also Magnus, L., *Epilepsia* (1999) 40(Suppl 6): S66-S72; Laird, M. A. & Gidal, B. E., *Annal Pharmacotherap* (2000) 34: 802-807; Nicholson, B., *Acta Neurol Scand* (2000) 101: 359-371).

Ziconotide (Prialt®; SNX-111) is a synthetic analgesic derived from the cone snail peptide *Conus magus* MVIIA that has been shown to reversibly block N-type calcium channels. In a variety of animal models, the selective block of N-type channels via intrathecal administration of Ziconotide significantly depresses the formalin phase 2 response, thermal hyperalgesia, mechanical allodynia and post-surgical pain (Malmberg, A. B. & Yaksh, T. L., *J Neurosci* (1994) 14: 4882-4890; Bowersox, S. S. et al., *J Pharmacol Exp Ther* (1996) 279: 1243-1249; Sluka, K. A., *J Pharmacol Exp Ther* (1998) 287: 232-237; Wang,Y-X. et al., *Soc Neurosci Abstr* (1998) 24: 1626).

Ziconotide has been evaluated in a number of clinical trials via intrathecal administration for the treatment of a variety of conditions including post-herpetic neuralgia, phantom limb syndrome, HIV-related neuropathic pain and intractable cancer pain (reviewed in Mathur, V. S., *Seminars in Anesthesia, Perioperative medicine and Pain* (2000) 19: 67-75). In phase II and III clinical trials with patients unresponsive to intrathecal opiates, Ziconotide has significantly reduced pain scores and in a number of specific instances resulted in relief after many years of continuous pain. Ziconotide is also being examined for the management of severe post-operative pain as well as for brain damage following stroke and severe head trauma (Heading, C., *Curr Opin CPNS Investigational Drugs* (1999) 1: 153-166). In two case studies Ziconotide has been further examined for usefulness in the management of intractable spasticity following spinal cord injury in patients unresponsive to baclofen and morphine (Ridgeway, B. et al., *Pain* (2000) 85: 287-289). In one instance Ziconotide decreased the spasticity from the severe range to the mild to none range with few side effects. In another patient Ziconotide also reduced spasticity to the mild range although at the required dosage significant side effects including memory loss, confusion and sedation prevented continuation of the therapy.

T-type calcium channels are involved in various medical conditions. In mice lacking the gene expressing the $\alpha_{1G}$ subunit, resistance to absence seizures was observed (Kim, C. et al., *Mol Cell Neurosci* (2001) 18(2): 235-245). Other studies have also implicated the $\alpha_{1H}$ subunit in the development of epilepsy (Su, H. et al., *J Neurosci* (2002) 22: 3645-3655). There is strong evidence that some existing anticonvulsant drugs, such as ethosuximide, function through the blockade of T-type channels (Gomora, J. C. et al., *Mol Pharmacol* (2001) 60: 1121-1132).

Low voltage-activated calcium channels are highly expressed in tissues of the cardiovascular system. Mibefradil, a calcium channel blocker 10-30-fold selective for T-type over L-type channels, was approved for use in hypertension and angina. It was withdrawn from the market shortly after launch due to interactions with other drugs (Heady, T. N., et al., *Jpn J Pharmacol.* (2001) 85:339-350).

Growing evidence suggests T-type calcium channels may also be involved in pain. Both mibefradil and ethosuximide have shown anti-hyperalgesic activity in the spinal nerve ligation model of neuropathic pain in rats (Dogrul, A., et al., *Pain* (2003) 105:159-168).

U.S. Pat. Nos. 6,011,035; 6,294,533; 6,310,059; and 6,492, 375; PCT publications WO 01375 and WO 01/45709; PCT publications based on PCT CA 99/00612, PCT CA 00/01586; PCT CA 00/01558; PCT CA 00/01557; PCT CA 2004/ 000535; and PCT CA 2004/000539, and U.S. patent application Ser. No. 10/746,932 filed 23 Dec. 2003; Ser. No. 10/746, 933 filed 23 Dec. 2003; Ser. No. 10/409,793 filed 8 Apr. 2003; Ser. No. 10/409,868 filed 8 Apr. 2003; Ser. No. 10/655,393 filed 3 Sep. 2003; Ser. No. 10/821,584 filed 9 Apr. 2004; and Ser. No. 10/821,389 filed 9 Apr. 2004 disclose calcium channel blockers where a piperidine or piperazine ring is substituted by various aromatic moieties.

U.S. Pat. No. 5,646,149 describes calcium channel antagonists of the formula A-Y-B wherein B contains a piperazine or piperidine ring directly linked to Y. An essential component of these molecules is represented by A, which must be an antioxidant; the piperazine or piperidine itself is said to be important. The exemplified compounds contain a benzhydryl substituent, based on known calcium channel blockers (see below). U.S. Pat. No. 5,703,071 discloses compounds said to be useful in treating ischemic diseases. A mandatory portion of the molecule is a tropolone residue, with substituents such as piperazine derivatives, including their benzhydryl derivatives. U.S. Pat. No. 5,428,038 discloses compounds indicated to exhibit a neural protective and antiallergic effect. These compounds are coumarin derivatives which may include derivatives of piperazine and other six-membered heterocycles. A permitted substituent on the heterocycle is diphenylhydroxymethyl. U.S. Pat. No. 6,458,781 describes 79 amides as calcium channel antagonists though only a couple of which contain both piperazine rings and benzhydryl moieties. Thus, approaches in the art for various indications which may involve calcium channel blocking activity have employed compounds which incidentally contain piperidine or piperazine moieties substituted with benzhydryl but mandate additional substituents to maintain functionality.

Certain compounds containing both benzhydryl moieties and piperidine or piperazine are known to be calcium channel antagonists and neuroleptic drugs. For example, Gould, R. J., et al., *Proc Natl Acad Sci USA* (1983) 80:5122-5125 describes antischizophrenic neuroleptic drugs such as lidoflazine, fluspirilene, pimozide, clopimozide, and penfluridol. It has also been shown that fluspirilene binds to sites on L-type calcium channels (King, V. K., et al., *J Biol Chem* (1989) 264:5633-5641) as well as blocking N-type calcium current (Grantham, C. J., et al., *Brit J Pharmacol* (1944) 111:483-488). In addition, Lomerizine, as developed by Kanebo, K. K., is a known calcium channel blocker. However, Lomerizine is not specific for N-type channels. A review of publications concerning Lomerizine is found in Dooley, D., *Current Opinion in CPNS Investigational Drugs* (1999) 1:116-125.

All patents, patent applications and publications are herein incorporated by reference in their entirety.

DISCLOSURE OF THE INVENTION

The invention relates to compounds useful in treating conditions such as stroke, anxiety, overactive bladder, inflammatory bowel disease, irritable bowel syndrome, interstitial colitis, head trauma, migraine, chronic, neuropathic and acute pain, drug and alcohol addiction, neurodegenerative disorders, psychoses, sleep disorders, depression, epilepsy, diabetes, cancer, male contraception, hypertension, pulmonary hypertension, cardiac arrhythmias, congestive heart failure, angina pectoris and other indications associated with calcium metabolism, including synaptic calcium channel-mediated functions.

The compounds of the invention are of the formula

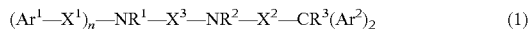

$$(Ar^1\!-\!X^1)_n\!-\!NR^1\!-\!X^3\!-\!NR^2\!-\!X^2\!-\!CR^3(Ar^2)_2 \qquad (1)$$

wherein each $Ar^1$ is independently a cyclic moiety which is aromatic or nonaromatic, carbocyclic or heterocyclic wherein heterocyclic forms of $Ar^1$ contain 1-3 heteroatoms selected from O, S and N;

$X^1$ is a linker comprising a chain of 1-5 members;

n is 1 or 2;

$R^1$ is absent when n is 2 and when n is 1, $R^1$ is H, alkyl (1-8C), alkenyl (2-8C) or alkynyl (2-8C);

$X^3$ is alkylene, alkenylene or alkynylene (2-8C);

$R^2$ is H, alkyl (1-8C), alkenyl (2-8C) or alkynyl (2-8C);

$X^2$ is a linker comprising a chain of 2-9 members;

$R^3$ is H, OH or alkyl (1-4C);

each $Ar^2$ independently comprises a 6-membered aromatic ring optionally containing 1-3 nitrogen atoms;

wherein each $Ar^1$ and $Ar^2$ in formula (1) may be unsubstituted or substituted by one or more substituents selected from the group consisting of =O (in nonaromatic cyclic moieties), alkyl (1-8C), alkenyl (2-8C), alkynyl (2-8C), aryl, alkylaryl, halo, $CHF_2$, $CF_3$, $OCF_3$, $OCHF_2$, CN, $NO_2$, $NR_2$, OR, SR, COR, COOR, $CONR_2$, SOR, $SO_2R$, $SO_3R$, $SONR_2$, $SO_2NR_2$, $SO_3NR_2$, NROCR, OOCR, NRSOR, $NRSO_2R$, and $NRSO_3R$, wherein R is H, alkyl (1-8C), alkenyl (2-8C), alkynyl (2-8C), aryl, or alkylaryl or heteroforms of any of the foregoing, each of which may optionally be substituted; and wherein two R on the same N may form a 5-7 membered ring, and wherein two substituents on adjacent atoms may form a 5-7 membered ring; and wherein the chain comprised in $X^1$ and $X^2$ may be substituted by =O, alkyl (1-8C), alkenyl (2-8C), alkynyl (2-8C), halo, $CHF_2$, $CF_3$, $OCF_3$, $OCHF_2$, CN, $NO_2$, $NR_2$, OR, SR, COR, COOR, $CONR_2$, SOR, $SO_2R$, $SO_3R$, $SONR_2$, $SO_2NR_2$, $SO_3NR_2$, NROCR, OOCR, NRSOR; $NRSO_2R$ and/or $NRSO_3R$, wherein R is H or alkyl (1-8C), alkenyl (2-8C), alkynyl (2-8C), aryl, or alkylaryl or heteroforms of any of the foregoing, each of which may optionally be substituted, and wherein two R on the same N may form a 5-7 membered ring, and wherein two substituents on adjacent atoms may form a 5-7 membered ring.

The compounds of formula (1) may also be provided in the form of salts or conjugates.

The invention is also directed to methods to modulate calcium channel activity, preferably N-type and T-type channel activity, using the compounds of formula (1). These compounds, thus, can be used to treat certain undesirable physiological conditions; these conditions are associated with calcium channel activity. The invention is also directed to the use of these compounds for the preparation of medicaments for the treatment of conditions requiring modulation of calcium channel activity, including stroke, anxiety, overactive bladder, inflammatory bowel disease, irritable bowel syndrome, interstitial colitis, head trauma, migraine, chronic, neuropathic and acute pain, drug and alcohol addiction, neurodegenerative disorders, psychoses, depression, epilepsy, diabetes, cancer, male contraception, hypertension, pulmonary hypertension, cardiac arrhythmias, congestive heart failure and angina pectoris. In another aspect, the invention is directed to pharmaceutical compositions containing the compounds of formula (1).

MODES FOR CARRYING OUT THE INVENTION

The compounds of formula (1) including compounds where the provisos do not apply are useful in the methods of the invention and exert their desirable effects through their ability to modulate the activity of N-type and/or T-type calcium channels. The compounds of formula (1) are particularly useful in modulating the activity of N-type calcium channels. This makes them useful for treatment of certain conditions. Conditions where modulation of N-type calcium channels is desired include: chronic and acute pain; mood disorders such as anxiety, depression, and addiction; neurodegenerative disorders; gastrointestinal disorders such as inflammatory bowel disease and irritable bowel syndrome; genitourinary disorders such as urinary incontinence, interstitial colitis and sexual dysfunction; neuroprotection such as cerebral ischemia, stroke and traumatic brain injury; and metabolic disorders such as diabetes and obesity. Conditions where modulation of T-type calcium channels is desired include: cardiovascular disease; epilepsy; diabetes; certain types of cancer such as prostate cancer; chronic and acute pain; sleep disorders; Parkinson's disease; psychosis such as schizophrenia; and male birth control.

Acute pain as used herein includes but is not limited to nociceptive pain and post-operative pain. Chronic pain includes but is not limited by: peripheral neuropathic pain such as post-herpetic neuralgia, diabetic neuropathic pain, neuropathic cancer pain, failed back-surgery syndrome, trigeminal neuralgia, and phantom limb pain; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome; inflammatory pain such as rheumatoid arthritis and endometriosis; headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

Anxiety as used herein includes but is not limited to the following conditions: generalized anxiety disorder, social anxiety disorder, panic disorder, obsessive-compulsive disorder, and post-traumatic stress syndrome. Addiction includes but is not limited to dependence, withdrawal and/or relapse of cocaine, opioid, alcohol and nicotine.

Neurodegenerative disorders as used herein include Parkinson's disease, Alzheimer's disease, multiple sclerosis, neuropathies, Huntington's disease and amyotrophic lateral sclerosis (ALS).

Cardiovascular disease as used herein includes but is not limited to hypertension, pulmonary hypertension, arrhythmia (such as atrial fibrillation and ventricular fibrillation), congestive heart failure, and angina pectoris.

Epilepsy as used herein includes but is not limited to partial seizures such as temporal lobe epilepsy, absence seizures, generalized seizures, and tonic/clonic seizures.

For greater certainty, in treating osteoarthritic pain, joint mobility will also improve as the underlying chronic pain is reduced. Thus, use of compounds of the present invention to treat osteoarthritic pain inherently includes use of such compounds to improve joint mobility in patients suffering from osteoarthritis.

While the compounds described above generally have this activity, availability of this class of calcium channel modulators permits a nuanced selection of compounds for particular disorders. The availability of this class of compounds provides not only a genus of general utility in indications that are affected by calcium channel activity, but also provides a large number of compounds which can be mined and manipulated for specific interaction with particular forms of calcium channels. Compounds may be active against both N-type and T-type calcium channels and that may be of particular benefit for certain disorders, particularly those indications modulated by both N-type and T-type calcium channels. However, for some indications, it may be desirable to have a compound that selectively modulates N-type or T-type calcium channels. The availability of recombinantly produced calcium channels of the $\alpha_{1A}$-$\alpha_{1I}$ and $\alpha_{1S}$ types set forth above, facilitates this selection process. Dubel, S. J., et al., *Proc. Natl. Acad. Sci. USA* (1992) 89:5058-5062; Fujita, Y., et al., *Neuron* (1993) 10:585-598; Mikami, A., et al., *Nature* (1989) 340:230-233; Mori, Y., et al., *Nature* (1991) 350:398-402; Snutch, T. P., et al., *Neuron* (1991) 7:45-57; Soong, T. W., et al., *Science* (1993) 260:1133-1136; Tomlinson, W. J., et al., *Neuropharmacology* (1993) 32:1117-1126; Williams, M. E., et al., *Neuron* (1992) 8:71-84; Williams, M. E., et al., *Science* (1992) 257:389-395; Perez-Reyes, et al., *Nature* (1998) 391:896-900; Cribbs, L. L., et al., *Circulation Research* (1998) 83:103-109; Lee, J. H., et al., *Journal of Neuroscience* (1999) 19:1912-1921; McRory, J. E., et al., *Journal of Biological Chemistry* (2001) 276:3999-4011.

It is known that calcium channel activity is involved in a multiplicity of disorders, and particular types of channels are associated with particular conditions. The association of N-type and T-type channels in conditions associated with neural transmission would indicate that compounds of the invention which target N-type or T-type channels are most useful in these conditions. Many of the members of the genus of compounds of formula (1) exhibit high affinity for N-type channels and/or T-type channels. Thus, as described below, they are screened for their ability to interact with N-type and/or T-type channels as an initial indication of desirable function. It is desirable that the compounds exhibit $IC_{50}$ values of <1 µM. The $IC_{50}$ is the concentration which inhibits 50% of the calcium, barium or other permeant divalent cation flux at a particular applied potential.

There are three distinguishable types of calcium channel inhibition. The first, designated "open channel blockage," is conveniently demonstrated when displayed calcium channels are maintained at an artificially negative resting potential of about −100 mV (as distinguished from the typical endogenous resting maintained potential of about −70 mV). When the displayed channels are abruptly depolarized under these conditions, calcium ions are caused to flow through the channel and exhibit a peak current flow which then decays. Open channel blocking inhibitors diminish the current exhibited at the peak flow and can also accelerate the rate of current decay.

This type of inhibition is distinguished from a second type of block, referred to herein as "inactivation inhibition." When maintained at less negative resting potentials, such as the physiologically important potential of −70 mV, a certain percentage of the channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of receptors that are in an inactivated state.

A third type of inhibition is designated "resting channel block". Resting channel block is the inhibition of the channel that occurs in the absence of membrane depolarization, that would normally lead to opening or inactivation. For example, resting channel blockers would diminish the peak current amplitude during the very first depolarization after drug application without additional inhibition during the depolarization.

In order to be maximally useful in treatment, it is also helpful to assess the side reactions which might occur. Thus, in addition to being able to modulate a particular calcium channel, it is desirable that the compound has very low activity with respect to the HERG $K^+$ channel which is expressed in the heart. Compounds that block this channel with high potency may cause reactions which are fatal. Thus, for a compound that modulates the calcium channel, it should also be shown that the HERG $K^+$ channel is not inhibited. Similarly, it would be undesirable for the compound to inhibit cytochrome p450 since this enzyme is required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The compounds of the invention modulate the activity of calcium channels; in general, said modulation is the inhibition of the ability of the channel to transport calcium. As described below, the effect of a particular compound on calcium channel activity can readily be ascertained in a routine assay whereby the conditions are arranged so that the channel is activated, and the effect of the compound on this activation (either positive or negative) is assessed. Typical assays are described hereinbelow.

The Invention Compounds

The components of formula (1) are described above. Further definition may be useful.

As used herein, the term "alkyl," "alkenyl" and "alkynyl" include straight-chain, branched-chain and cyclic monovalent substituents, containing only C and H when they are unsubstituted or unless otherwise noted. They may be substituted or unsubstituted. Examples include methyl, ethyl, isobutyl, cyclohexyl, cyclopentylethyl, 2-propenyl, 3-butynyl, and the like. Typically, the alkyl, alkenyl and alkynyl substituents contain 1-10C or 1-8C (alkyl) or 2-10C or 2-8C (alkenyl or alkynyl). Preferably they contain 1-6C or 1-4C (lower alkyl) or 2-6C or 2-4C (lower alkenyl or lower alkynyl).

The "heteroforms," i.e., heteroalkyl, heteroalkenyl, and heteroalkynyl, are similarly defined but may contain one or more O, S or N heteroatoms or combinations thereof within the backbone residue represented by alkyl, alkenyl, and alkynyl.

As used herein, "acyl" encompasses the definitions of alkyl, alkenyl, alkynyl, each of which is coupled to an additional residue through a carbonyl group. Heteroacyl includes the related heteroforms.

As used in the present application, similarly, alkylene, alkenylene and alkynylene linkers are bivalent chains of carbon atoms, and may be straight chain, branched chain or cyclic and may be substituted or unsubstituted unless otherwise noted. Their heteroforms, heteroalkylene, heteroalkenylene, and heteroalkynylene, are similarly defined but one or more C in this claim is substituted by O, S and/or N. The linkers represented by $X^3$ herein are unsubstituted, and do not include the heteroforms.

"Aromatic" moiety or "aryl" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of up to 8C, or the heteroforms thereof. These chains may also include a carbonyl group, thus making them able to provide substituents as an arylacyl or arylheteroacyl, heteroarylheteroacyl, or heteroarylacyl moiety.

In general, any alkyl, alkenyl, alkynyl, acyl, or aryl (including the heteroforms) group defined in substituents may themselves optionally be substituted by additional substituents. The nature of these additional substituents is similar to that recited with regard to the primary substituents themselves. Thus, for example, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included.

Non-interfering substituents in general include, but are not limited to, alkyl, alkenyl, alkynyl, aryl, arylalkyl, acyl, =O, halo, OR, $NR_2$, SR, —SOR, —$SO_2R$, $SO_2R$, —OCOR, —NRCOR, —$NRCONR_2$, —NRCOOR, —$OCONR_2$, —RCO, —COOR, NRSOR, $NRSO_2R$, $NRSO_3R$, —$CONR_2$, SONR, $SO_2NR_2$, and $SO_3NR_2$ (wherein each R is independently H or alkyl (1-8C), alkenyl (2-8C), alkenyl (2-8C), aryl or arylalkyl, or the heteroatom-containing forms of any of these), —CN, —$CF_3$, and $NO_2$, and like substituents.

In the compounds of the invention, Ar is preferably optionally substituted phenyl, 2-, 3- or 4-pyridyl, indolyl, 2- or 4-pyrimidyl, pyridazinyl, benzotriazolyl or benzimidazolyl. More preferably Ar is phenyl, pyridyl, or pyrimidyl. Most preferably Ar is phenyl. Each of these embodiments may optionally be substituted with one or more groups defined above, including but not limited to alkyl, alkenyl, alkynyl, aryl, O-aryl, O-alkylaryl, O-aroyl, NR-aryl, N-alkylaryl, NR-aroyl, halo, OR, $NR_2$, SR, —OOCR, —NROCR, RCO, —COOR, —$CONR_2$, and/or $SO_2NR_2$, wherein each R is independently H or alkyl (1-8C), alkenyl (2-8C), alkynyl (2-8C), aryl or alkylaryl, or their heteroforms and/or by —CN, —$CF_3$, and/or $NO_2$. Alkyl, alkenyl, alkynyl and aryl portions of these may be further substituted by similar substituents, as set forth above.

In either of the instances described above, two R groups on the same nitrogen atom may form a ring, and two R groups on adjacent carbons may form a ring. These rings would have 5-7 members.

Preferred embodiments of $Ar^1$ include 2-, 3-, 4-, pyridyl, pyrimidyl, and phenyl; similarly, $Ar^2$ comprises these preferred forms, particularly phenyl residues. Preferred substituents on each $Ar^1$ and $Ar^2$ include alkyl, $CF_3$, $CHF_2$, OR, SR, $NR_2$, where R is as above-defined, and halo. Particularly preferred alkyl substituents include tertiary butyl, isopropyl and methyl; particularly preferred substituents of the formula OR include those wherein R is alkyl, especially methyl. Preferred substituents on $Ar^2$ are similar to those set forth above and particularly preferred is halo, especially para fluoro.

Important embodiments of the linkers described as $X^1$ include those wherein a carbonyl group is adjacent the nitrogen depicted, in particular $X^1$ may be CO per se, or is alkylene or heteroalkylene, particularly where C=O is adjacent said N, but also including alkylene per se, and heteroalkylene per se, particularly containing one heteroatom which is S, N or O. In one set of embodiments the heteroatom is O. In embodiments where n is 2, one group of compounds of the invention includes instances wherein both $X^1$ are identical or wherein both $Ar^1$ are identical or where both $Ar^1$—$X^1$ are identical.

$R^1$ and $R^2$ in one set of embodiments are independently H or lower alkyl (1-4C) and in a further set of embodiments, both $R^2$ and $R^1$ (if present) are H.

In one set of embodiments, $X^3$ is but-2-enyl or pent-2-enyl; the π bond contained may be in cis or trans form. In another set of embodiments, $X^3$ is but-2-ynyl or pent-2-ynyl; in still another set of embodiments, $X^3$ is of the formula $(CH_2)_m$ wherein m is 2-5.

In one set of the compounds of the invention $R^3$ is H or methyl; in many compounds, $R^3$ is H.

In one set of embodiments, both $Ar^2$ are identical and are pyridyl or phenyl, in particular phenyl. Preferred substituents are those as described for $Ar^1$, but with an important group comprising halo substituents, in particular para fluoro substituents. In one set of embodiments, the substituents on both $Ar^2$ are identical, and/or the rings of both $Ar^2$ are identical.

In the compounds of the invention, $X^2$ is alkylene, alkenylene or alkynylene of 2-9 carbons, including heteroforms thereof wherein one or more of said carbons is replaced by a heteroatom selected from the group consisting of O, S and N. In a preferred set of embodiments, $X^3$ contains a C=O substituent adjacent the nitrogen shown coupled to $X^2$. Particularly preferred are embodiments wherein $X^3$ is alkylene (2-9C) substituted by =O at the position adjacent N, and otherwise unsubstituted.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Suitable pharmaceutically acceptable acids and bases are well-known in the art, such as hydrochloric, sulphuric, citric, acidic, or tartaric acids and potassium hydroxide, sodium hydroxide, ammonium hydroxide, caffeine, various amines, and the like. Methods for preparation of the appropriate salts are well-established in the art.

In some cases, the compounds of the invention contain one or more chiral centers. The invention includes the isolated stereoisomeric forms as well as mixtures of stereoisomers in varying degrees of chiral purity.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to the compounds of formula (1) when modified so as to be included in a conjugate of this type.

Synthesis of the Invention Compounds

The compounds of the invention may be synthesized using conventional methods.

Reaction Scheme 1 may be used to prepare compounds containing an ethynyl group linking the amines.

Reaction Scheme 1

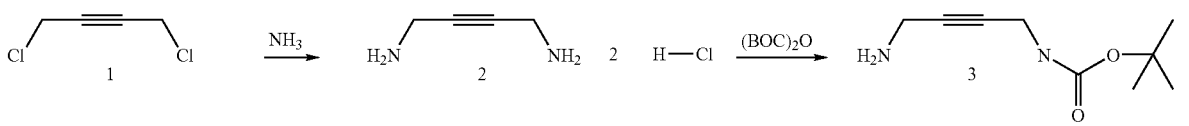

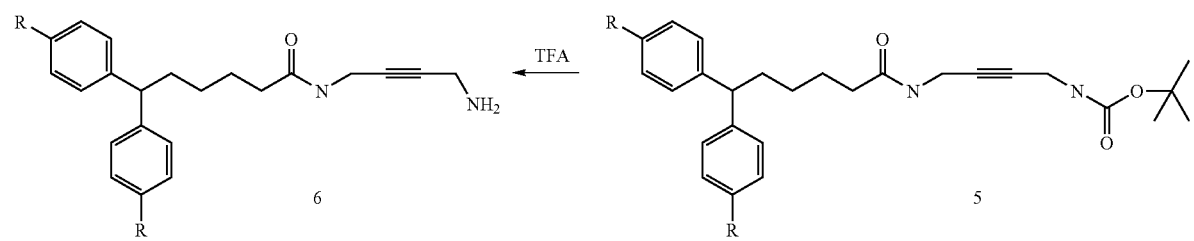

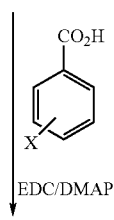

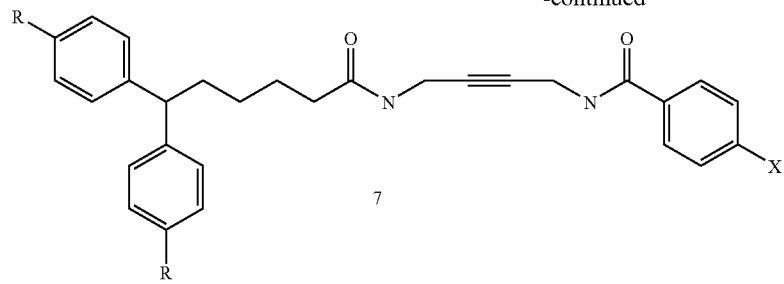
Reaction Scheme 2 may be used to prepare compounds containing a trans-ethenyl group linking the amines.
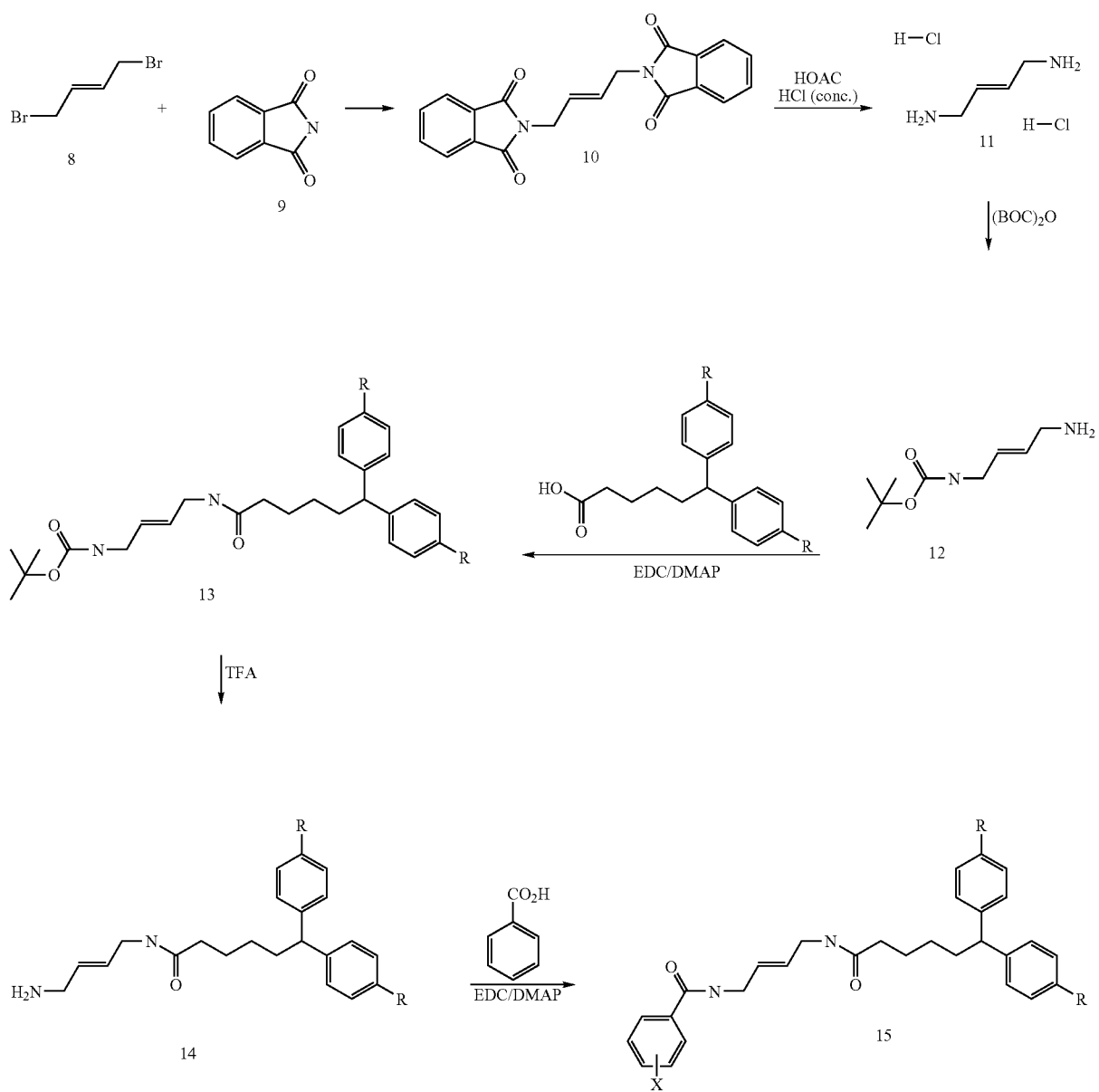

Reaction Scheme 3 may be used to prepare compounds containing a cis-ethenyl group linking the amines.

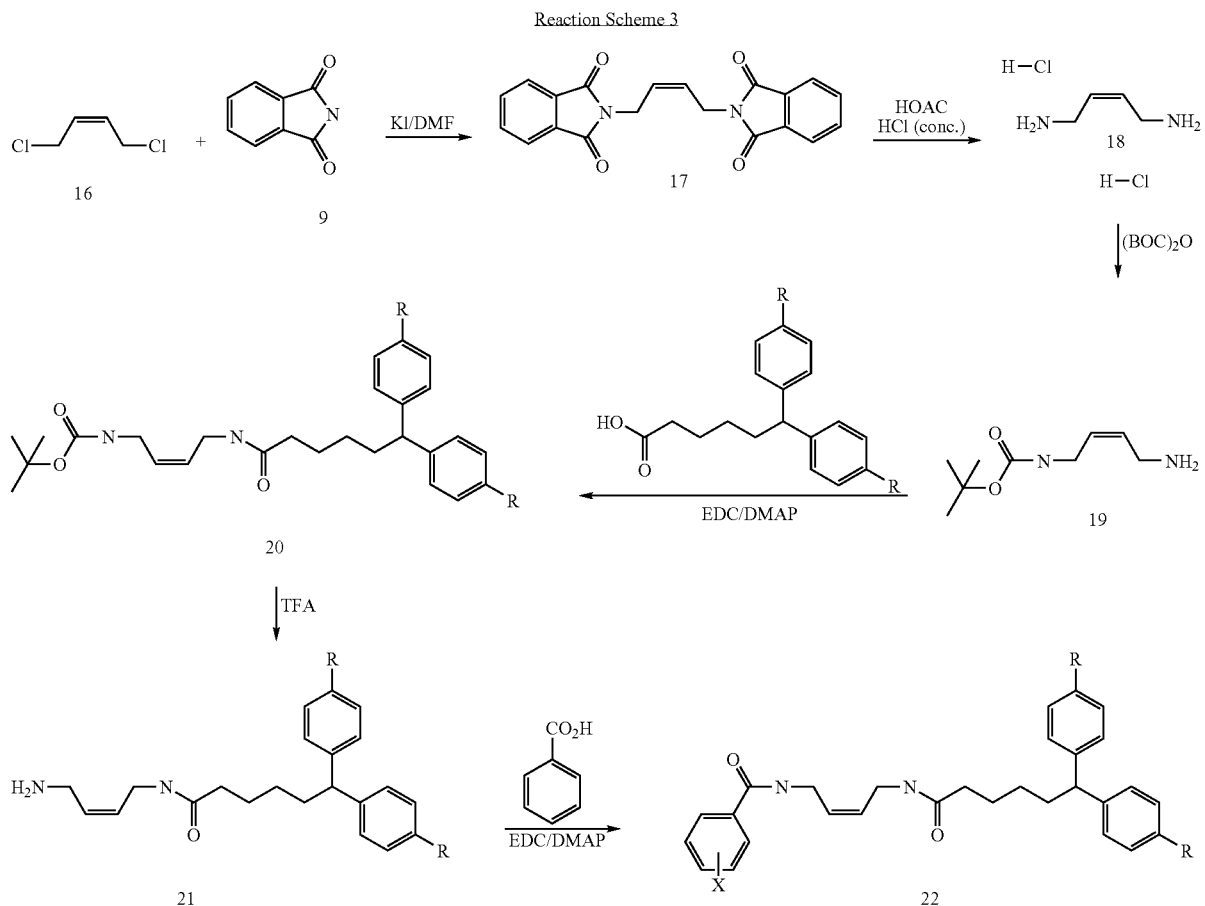

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P., et al., *Current Opinion in Biol.* (1993) 9:109-115; Salemme, F. R., et al., *Structure* (1997) 5:319-324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel, e.g., the N-type or T-type channel. In addition, using standard screening protocols, the libraries may be screened for compounds which block additional channels or receptors such as sodium channels, potassium channels and the like.

Methods of performing these screening functions are well known in the art. These methods can also be used for individually ascertaining the ability of a compound to agonize or antagonize the channel. Typically, the channel to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the channel is measured in the presence of calcium, barium or other permeant divalent cation and the ability of the compound to interfere with the signal generated is measured using standard techniques. In more detail, one method involves the binding of radiolabeled agents that interact with the calcium channel and subsequent analysis of equilibrium binding measurements including, but not limited to, on rates, off rates, $K_d$ values and competitive binding by other molecules.

Another method involves the screening for the effects of compounds by electrophysiological assay whereby individual cells are impaled with a microelectrode and currents through the calcium channel are recorded before and after application of the compound of interest.

Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel or as resting channel blockers.

The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.03 Hz. Finally, resting channel blockers would diminish the peak current amplitude during the very first depolarization after drug application without additional inhibition during the depolarization.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, Pa., incorporated herein by reference.

In general, for use in treatment, the compounds of formula (1) may be used alone, as mixtures of two or more compounds of formula (1) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.1-15 mg/kg, preferably 0.1-1 mg/kg. However, dosage levels are highly dependent on the nature of the condition, drug efficacy, the condition of the patient, the judgment of the practitioner, and the frequency and mode of administration.

The following examples are intended to illustrate but not to limit the invention.

EXAMPLE 1

Synthesis of N-{4-[6,6-bis-(4-fluoro-phenyl)-hexanoylamino]-but-2-ynyl}-4-chloro-benzamide (P28)

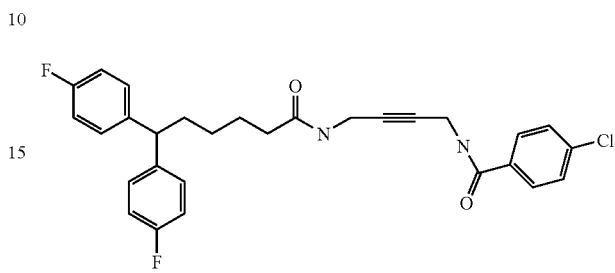

A. Synthesis of But-2-yne-1,4-diamine

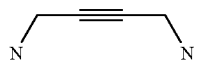

But-2-yne-1,4-dichloride (5 g, 40.67 mmol) and ammonium hydroxide (30%, 180 ml) were mixed and resulting solution stirred at room temperature overnight. The ammonia was then evaporated and the residue dissolved in water twice and evaporated. 1N HCl (20 ml) was added and evaporated to dryness. To the residue acetone was added and precipitate was filtered off and dried to give 9.5 g of desired crude product.

B. Synthesis of (4-Amino-but-2-ynyl)-carbamic acid tert-butyl ester

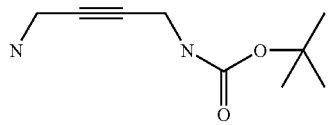

But-2-yne-1,4-diamine dihydrochloride (5.0 g, 31.84 mmol) was suspended in 10% TEA/MeOH solution (70 ml). To the above suspension TEA (8 ml) was added. A solution of di-tert-butyldicarbonate (2.31 g, 10.61 mmol) in methanol (5 ml) was added drop-wise to the vigorously stirred mixture. The reaction mixture was refluxed for 3 h, and stirred at room temperature overnight. After the removal of the precipitate, the filtrate was evaporated to dryness. The crude residue was purified by column chromatography with $CH_2Cl_2$:MeOH (20:1) to give the desired product in 70% yield.

C. Synthesis of {4-[6,6-bis-(4-fluoro-phenyl)-hexanoylamino]-but-2-ynyl}-carbamic acid tert-butyl ester

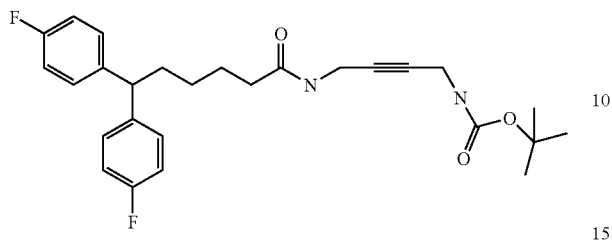

To a solution of (4-Amino-but-2-ynyl)-carbamic acid tert-butyl ester (0.8 g, 4.34 mmol) in dry $CH_2Cl_2$ (40 ml) was added 6,6-bis-(4-fluorophenyl)-hexanoic acid (1.32 g, 4.4 mmol) under nitrogen. To the reaction was added EDC (1.66 g, 8.68 mmol) and DMAP (cat) and the reaction mixture stirred under nitrogen at room temperature overnight. The reaction was then concentrated under reduced pressure. The residue dissolved in ethyl acetate: water (10:1) (150 ml). The organic was washed with water (30 ml, 2×) and 10% NaOH (30 ml) and dried over $MgSO_4$ and evaporated to dryness. The resulting residue was purified by column chromatography using $CH_2Cl_2$:$CH_3OH$ (15:1) to give the desired product in 72% yield.

D. Synthesis of 6,6-bis-(4-fluoro-phenyl)-hexanoic acid (4-amino-but-2-ynyl)-amide

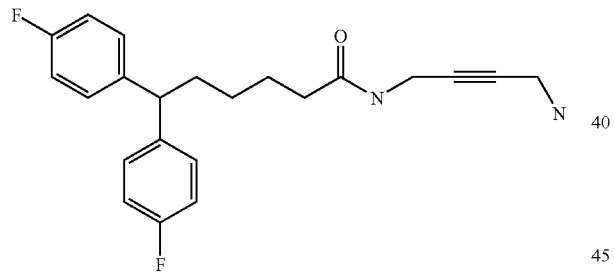

{4-[6,6-bis-(4-fluoro-phenyl)-hexanoylamino]-but-2-ynyl}-carbamic acid tert-butyl ester (1.6 g, 3.4 mmol) was dissolved in dry $CH_2Cl_2$ (50 ml) followed by addition of TFA (20 ml). The resulting solution was stirred at room temperature for 2 hrs. The solution was concentrated under reduced pressure. The resulting residue was dissolved in water (20 ml) and pH of the solution was adjusted to 10. The water phase was extracted with $CH_2Cl_2$ (100 ml), and dried over magnesium sulfate. The solvent was evaporated under reduced pressure to give the desired product in almost quantitative yield.

E. Synthesis of Final Product

To a solution of 6,6-bis-(4-fluoro-phenyl)-hexanoic acid (4-amino-but-2-ynyl)-amide (0.69 g, 1.86 mmol) in dry $CH_2Cl_2$ (40 ml) was added 4-chlorobenzoic acid (0.29 g, 1.86 mmol) under nitrogen. To the reaction was added EDC (0.71 g, 3.72 mmol) and DMAP (cat) and the reaction mixture stirred under nitrogen at room temperature overnight. The reaction was then concentrated under reduced pressure. The residue dissolved in ethyl acetate: water (10:1) (150 ml). The organic was washed with water (30 ml, 2×) and 10% NaOH (30 ml) and dried over $MgSO_4$ and evaporated to dryness. The resulting residue was purified by column chromatography using $CH_2Cl_2$:$CH_3OH$ (20:1) to give a desired product in good yield.

EXAMPLE 2

Synthesis of N-{4-[6,6-Bis-(4-fluoro-phenyl)-hexanoylamino]-but-2-enyl}-4-fluoro-benzamide (P10)

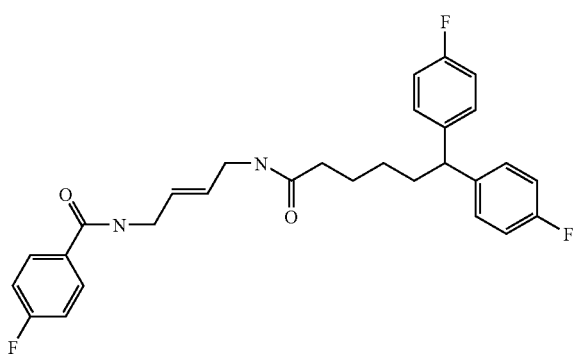

A. Synthesis of (E)-1,4-Diaminobut-2-ene dihydrochloride

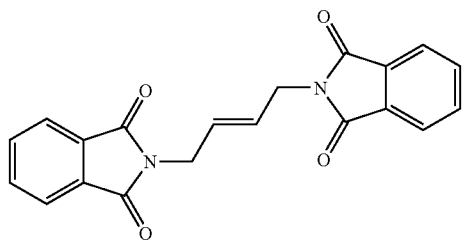

Potassium phathalimide (20 g, 108 mmol) was added in portions over 2 h to a stirred solution of (E)-1,4-dibromobut-2-ene (10.7 g, 50 mmol) in DMF (100 ml) at room temperature. The mixture was stirred for a further 3 days at this temperature, then poured into water (100 ml), and the mixture was extracted with dichloromethane (5×100 ml). The organic extracts were dried, filtered and concentrated in vacuo to leave DMF (ca. 30 ml), and a white solid, which was filtered off and washed with ether (3×10 ml) to give (E)-1,4-diphathalimidobut-2-ene (15.5 g, 91% yield).

B. Synthesis of (E)-1,4-diaminobut-2-ene dihydrochloride

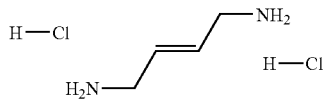

(E)-1,4-diphthalimidobut-2-ene (15.7 g, 45 mmol) was suspended in glacial acetic acid (160 ml), and conc. HCl (160 ml) was added. The mixture was heated at reflux until all the (E)-1,4-diphthalimidobut-2-ene had dissolved, then for further 24 h. The solution was cooled, filtered, and the solvent were concentrated in vacuo to ca. 10 ml. The precipitate was collected and washed with ether to afford (E)-1,4-diaminobut-2-ene dihydrochloride (6.5 g, 90% yield).

C. Synthesis of (4-amino-but-2-enyl)-carbamic acid tert-butyl ester

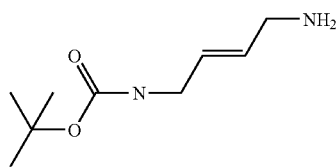

(E)-1,4-diaminobut-2-ene dihydrochloride (8.0 g, 50 mmol) was suspended in 10% TEA/MeOH solution (120 ml). To the above suspension TEA (14 ml) was added. A solution of di-tert-butyldicarbonate (3.7 g, 16.8 mmol) in methanol (10 ml) was added drop-wise to the vigorously stirred mixture. The reaction mixture was refluxed for 3 h, and stirred at room temperature overnight. After the removal of the precipitate, the filtrate was evaporated to dryness. The crude residue was purified by column chromatography with $CH_2Cl_2$:MeOH (20:1) to give 1.5 g of the desired product.

D. Synthesis of {4-[6,6-Bis-(4-fluoro-phenyl)-hexanoylamino]-but-2-enyl}-carbamic acid tert-butyl ester

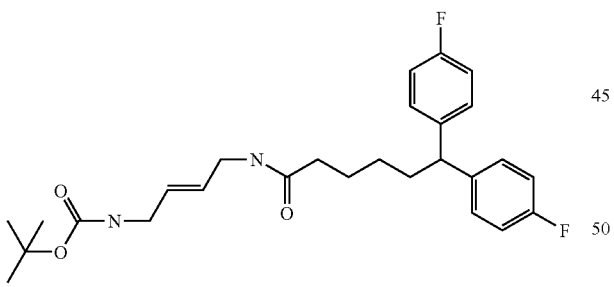

To a solution of (4-amino-but-2-enyl)-carbamic acid tert-butyl ester (1.0 g, 5.36 mmol) in dry $CH_2Cl_2$ (40 ml) was added 6,6-bis-(4-fluorophenyl)-hexanoic acid (1.62 g, 5.36 mmol) under nitrogen. To the reaction was added EDC (2.04 g, 10.72 mmol) and DMAP (cat) and the reaction mixture stirred under nitrogen at room temperature overnight. The reaction was then concentrated under reduced pressure. The residue dissolved in ethyl acetate:water (10:1) (150 ml). The organic was washed with water (30 ml, 2×) and 10% NaOH (30 ml) and dried over $MgSO_4$ and evaporated to dryness. The resulting residue was purified by column chromatography using $CH_2Cl_2$:$CH_3OH$ (15:1) to give the desired product in 70% yield.

E. Synthesis of 6,6-Bis-(4-fluoro-phenyl)-hexanoic acid (4-amino-but-2-enyl)-amide

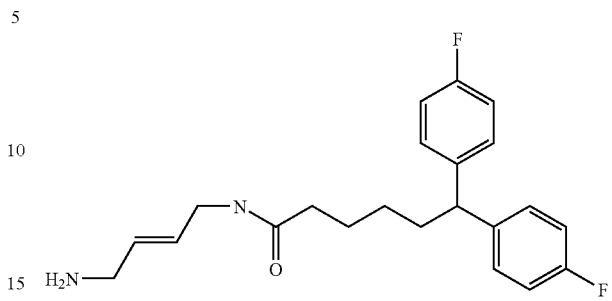

{4-[6,6-Bis-(4-fluoro-phenyl)-hexanoylamino]-but-2-enyl}-carbamic acid tert-butyl ester (1.6 g, 4.3 mmol) was dissolved in dry $CH_2Cl_2$ (50 ml) followed by addition of TFA (20 ml). The resulting solution was stirred at room temperature for 2 hrs. The solution was concentrated under reduced pressure. The resulting residue was dissolved in water (20 ml) and pH of the solution was adjusted to 10. The water phase was extracted with $CH_2Cl_2$ (100 ml), and dried over magnesium sulfate. The solvent was evaporated under reduced pressure to give the desired product in almost quantitative yield.

F. Synthesis of Final Product

To a solution of 6,6-Bis-(4-fluoro-phenyl)-hexanoic acid (4-amino-but-2-enyl)-amide (0.33 g, 0.89 mmol) in dry $CH_2Cl_2$ (30 ml) was added 4-fluoroobenzoic acid (0.13 g, 0.89 mmol) under nitrogen. To the reaction was added EDC (0.34 g, 1.78 mmol) and DMAP (cat) and the reaction mixture stirred under nitrogen at room temperature overnight. The reaction was then concentrated under reduced pressure. The residue dissolved in ethyl acetate:water (10:1) (150 ml). The organic was washed with water (25 ml, 2×) and 10% NaOH (25 ml) and dried over $MgSO_4$ and evaporated to dryness. The resulting residue was purified by column chromatography using $CH_2Cl_2$:$CH_3OH$ (20:1) to give a desired product in good yield.

EXAMPLE 3

Synthesis of (Z)-N-{4-[6,6-Bis-(4-fluoro-phenyl)-hexanoylamino]-but-2-enyl}-4-choloro-benzamide (P8)

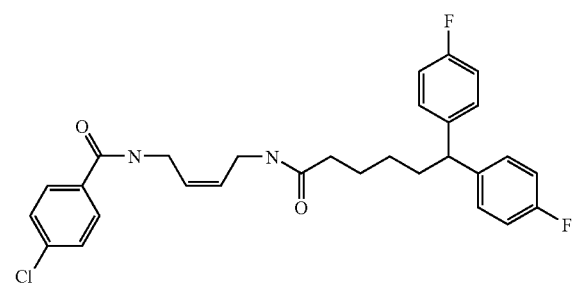

A. Synthesis of (Z)-6,6-Bis-(4-fluoro-phenyl)-hexanoic acid (4-amino-but-2-enyl)-amide

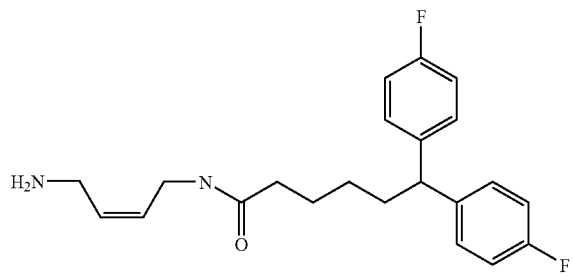

(Z)-{4-[6,6-Bis-(4-fluoro-phenyl)-hexanoylamino]-but-2-enyl}-carbamic acid tert-butyl ester (1.6 g, 4.3 mmol) was dissolved in dry $CH_2Cl_2$ (50 ml) followed by addition of TFA (20 ml). The resulting solution was stirred at room temperature for 2 hrs. The solution was concentrated under reduced pressure. The resulting residue was dissolved in water (20 ml) and pH of the solution was adjusted to 10. The water phase was extracted with $CH_2Cl_2$ (100 ml), and dried over magnesium sulfate. The solvent was evaporated under reduced pressure to give the desired product in almost quantitative yield.

B. Synthesis of Final Product

To a solution of 6,6-Bis-(4-fluoro-phenyl)-hexanoic acid (4-amino-but-2-enyl)-amide (0.33 g, 0.89 mmol) in dry $CH_2Cl_2$ (30 ml) was added 4-fluoroobenzoic acid (0.14 g, 0.89 mmol) under nitrogen. To the reaction was added EDC (0.34 g, 1.78 mmol) and DMAP (cat) and the reaction mixture stirred under nitrogen at room temperature overnight. The reaction was then concentrated under reduced pressure. The residue dissolved in ethyl acetate:water (10:1) (150 ml). The organic was washed with water (25 ml, 2×) and 10% NaOH (25 ml) and dried over $MgSO_4$ and evaporated to dryness. The resulting residue was purified by column chromatography using $CH_2Cl_2$:$CH_3OH$ (20:1) to give a desired product in 78% yield.

EXAMPLE 4

Following the procedures set forth, the following compounds were prepared:

| Compound No. | Chemical name | Structure |
|---|---|---|
| P1 | N-{(Z)-4-[6,6-Bis-(4-fluoro-phenyl)-hexanoylamino]-but-2-enyl}-3,4,5-trimethoxy-benzamide | 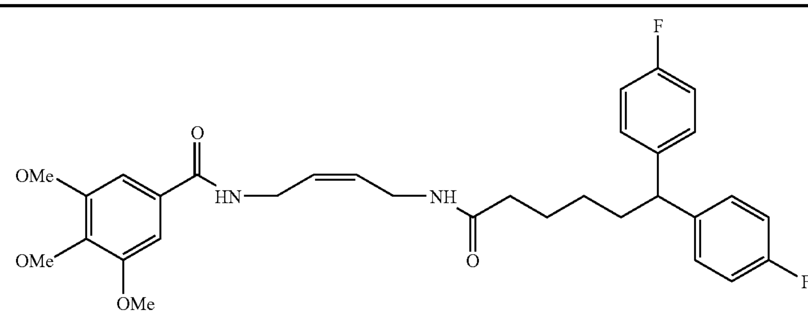 |
| P2 | N-{(Z)-4-[6,6-Bis-(4-fluoro-phenyl)-hexanoylamino]-but-2-enyl}-3,5-di-tert-butyl-4-methoxy-benzamide | 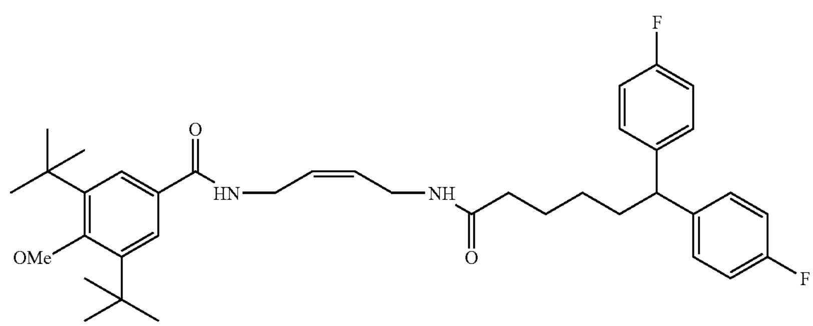 |
| P3 | N-{(Z)-4-[6,6-Bis-(4-fluoro-phenyl)-hexanoylamino]-but-2-enyl}-3,5-di-tert-butyl-4-hydroxy-benzamide | 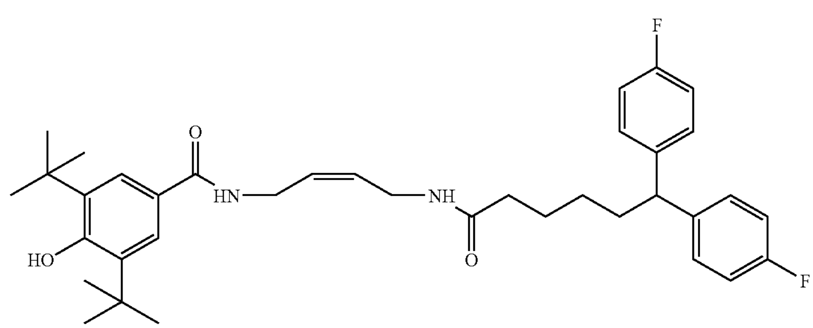 |

-continued

| Compound No. | Chemical name | Structure |
|---|---|---|
| P4 | N-{(Z)-4-[6,6-Bis-(4-fluoro-phenyl)-hexanoylamino]-but-2-enyl}-4-tert-butyl-benzamide | 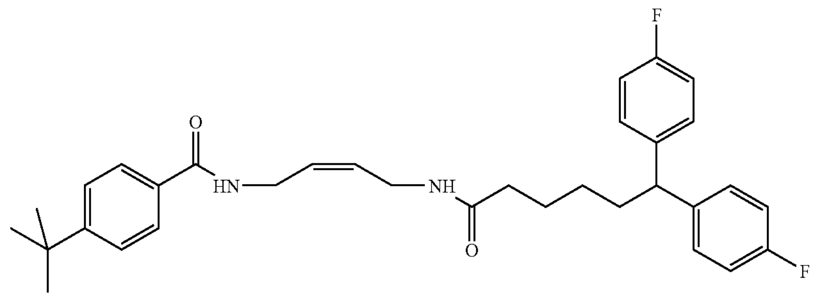 |
| P5 | N-{(Z)-4-[6,6-Bis-(4-fluoro-phenyl)-hexanoylamino]-but-2-enyl}-3,5-bis-trifluoromethyl-benzamide | 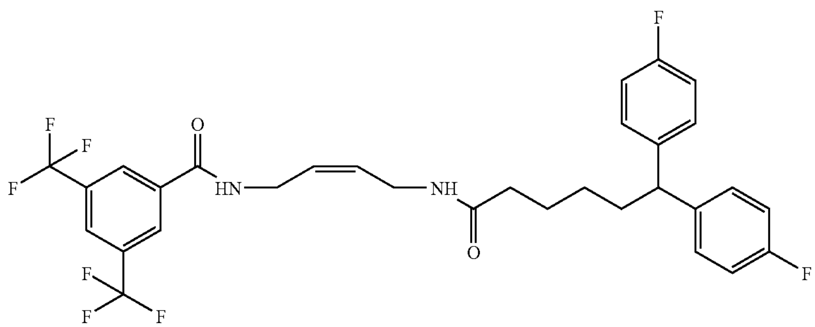 |
| P6 | 6,6-Bis-(4-fluoro-phenyl)-hexanoic acid{(Z)-4-[2-(4-chloro-phenoxy)-acetylamino]-but-2-enyl}-amide | 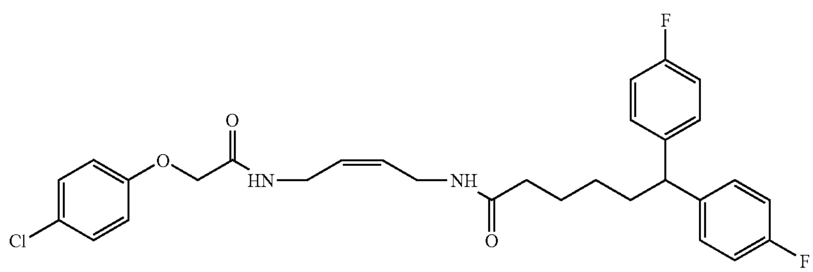 |
| P7 | N-{(Z)-4-[6,6-Bis-(4-fluoro-phenyl)-hexanoylamino]-but-2-enyl}-4-isopropyl-benzamide | 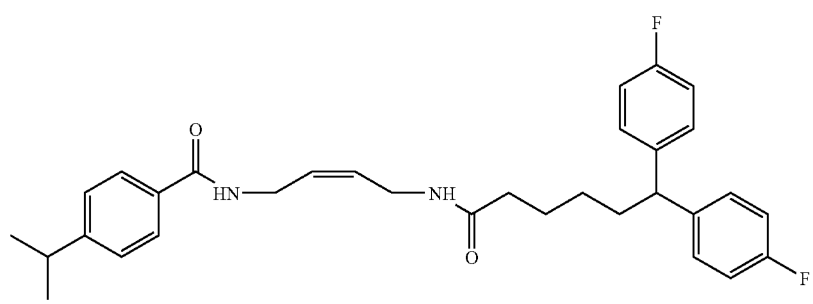 |
| P8 | N-{(Z)-4-[6,6-Bis-(4-fluoro-phenyl)-hexanoylamino]-but-2-enyl}-4-chloro-benzamide | 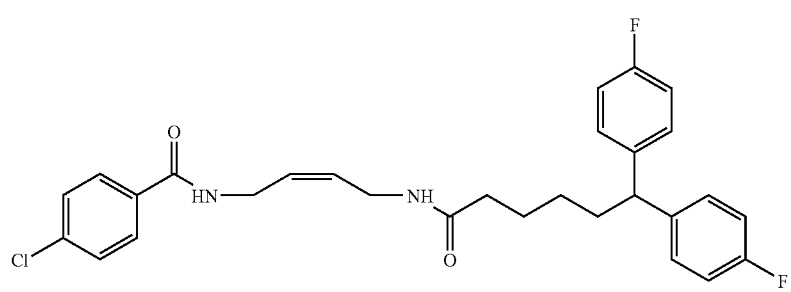 |

-continued

| Compound No. | Chemical name | Structure |
|---|---|---|
| P9 | N-{(Z)-4-[6,6-Bis-(4-fluoro-phenyl)-hexanoylamino]-but-2-enyl}-4-methyl-benzamide | 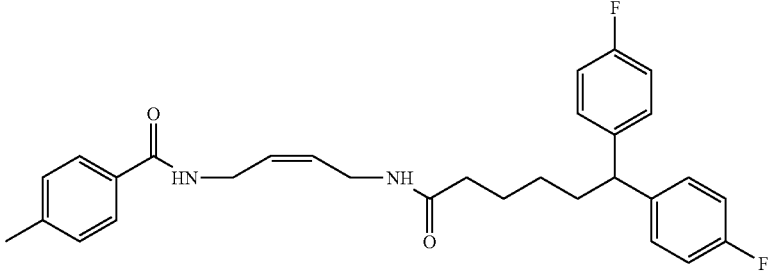 |
| P10 | N-{(Z)-4-[6,6-Bis-(4-fluoro-phenyl)-hexanoylamino]-but-2-enyl}-4-fluoro-benzamide | 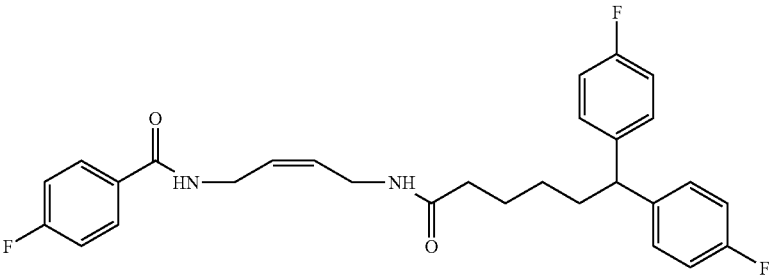 |
| P11 | N-{(E)-4-[6,6-Bis-(4-fluoro-phenyl)-hexanoylamino]-but-2-enyl}-3,4,5-trimethoxy-benzamide | 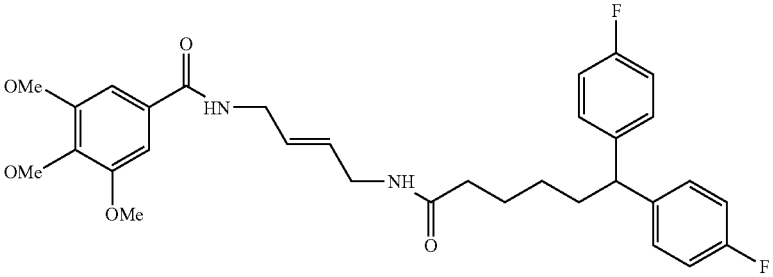 |
| P12 | N-{(E)-4-[6,6-Bis-(4-fluoro-phenyl)-hexanoylamino]-but-2-enyl}-3,5-di-tert-butyl-4-methoxy-benzamide | 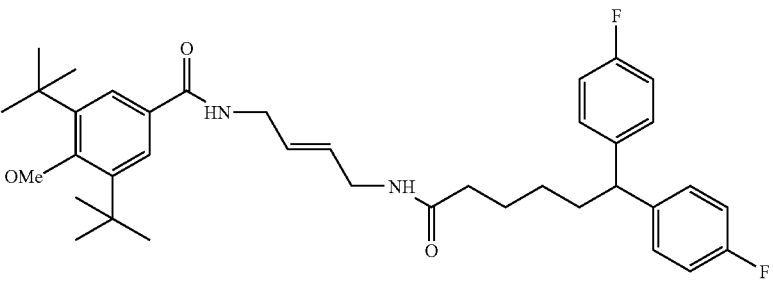 |
| P13 | N-{(E)-4-[6,6-Bis-(4-fluoro-phenyl)-hexanoylamino]-but-2-enyl}-3,5-di-tert-butyl-4-hydroxy-benzamide | 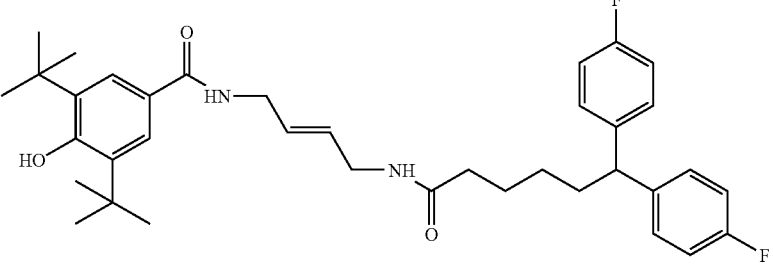 |

-continued

| Compound No. | Chemical name | Structure |
|---|---|---|
| P14 | N-{(E)-4-[6,6-Bis-(4-fluoro-phenyl)-hexanoylamino]-but-2-enyl}-4-tert-butyl-benzamide | 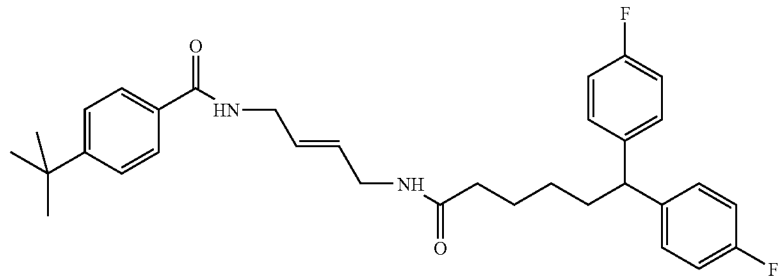 |
| P15 | N-{(E)-4-[6,6-Bis-(4-fluoro-phenyl)-hexanoylamino]-but-2-enyl}-3,5-bis-trifluoromethyl-benzamide | 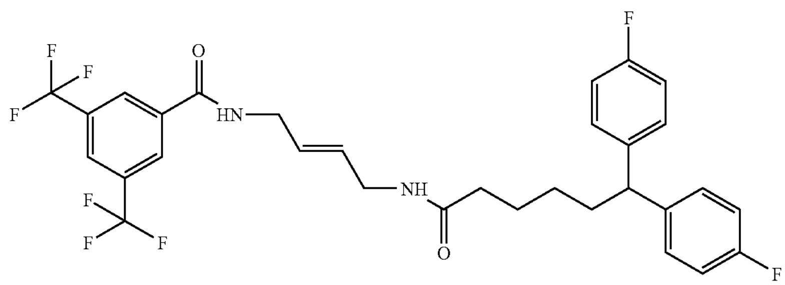 |
| P16 | 6,6-Bis-(4-fluoro-phenyl)-hexanoic acid{(E)-4-[2-(4-chloro-phenoxy)-acetylamino]-but-2-enyl}-amide | 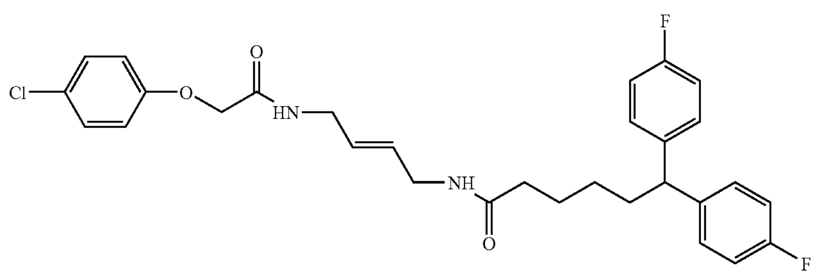 |
| P17 | N-{(E)-4-[6,6-Bis-(4-fluoro-phenyl)-hexanoylamino]-but-2-enyl}-4-isopropyl-benzamide | 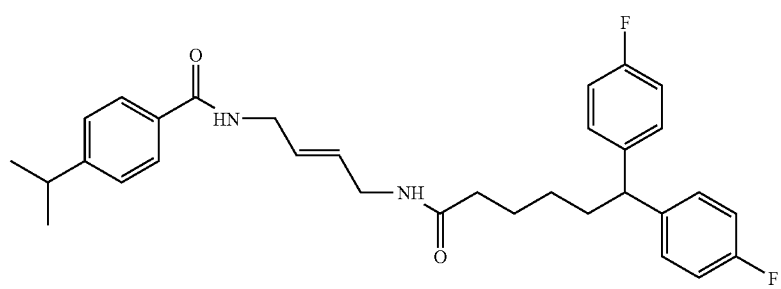 |
| P18 | N-{(E)-4-[6,6-Bis-(4-fluoro-phenyl)-hexanoylamino]-but-2-enyl}-4-chloro-benzamide | 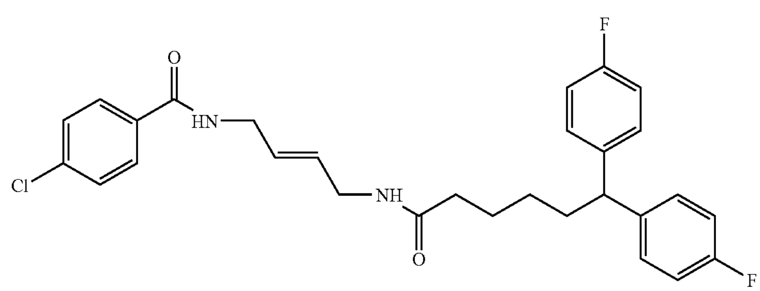 |

-continued

| Compound No. | Chemical name | Structure |
|---|---|---|
| P19 | N-{(E)-4-[6,6-Bis-(4-fluoro-phenyl)-hexanoylamino]-but-2-enyl}-4-methyl-benzamide | 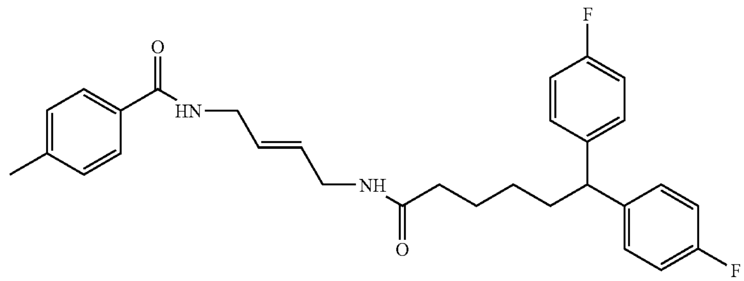 |
| P20 | N-{(E)-4-[6,6-Bis-(4-fluoro-phenyl)-hexanoylamino]-but-2-enyl}-4-fluoro-benzamide | 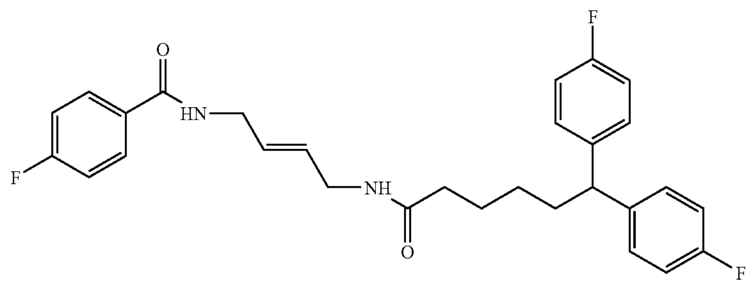 |
| P21 | N-[(E)-4-(Bis-pyridin-4-ylmethyl-amino)-but-2-enyl]-3,3-diphenyl-propionamide | 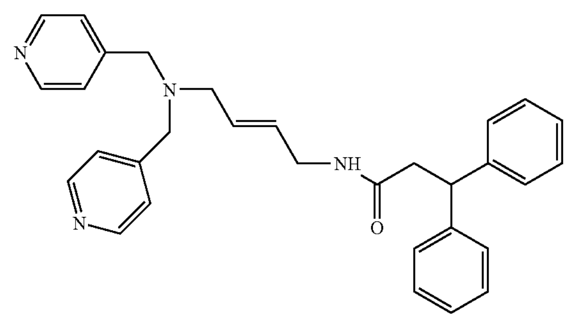 |
| P22 | N-{4-[6,6-Bis-(4-fluoro-phenyl)-hexanoylamino]-but-2-ynyl}-3,4,5-trimethoxy-benzamide | 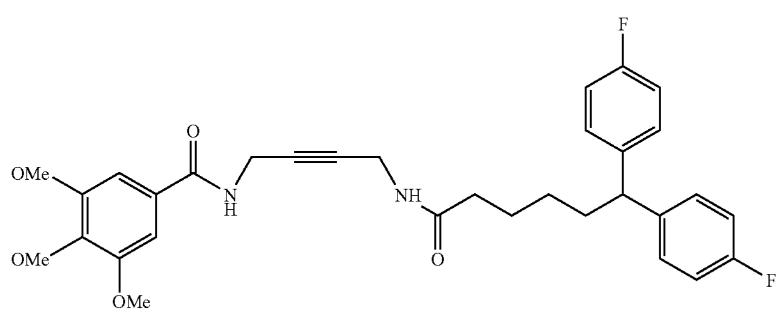 |
| P23 | N-{4-[6,6-Bis-(4-fluoro-phenyl)-hexanoylamino]-but-2-ynyl}-3,5-di-tert-butyl-4-methoxy-benzamide | 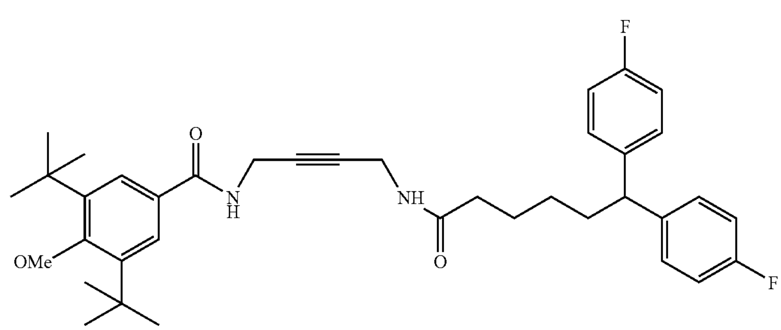 |

-continued

| Compound No. | Chemical name | Structure |
|---|---|---|
| P24 | N-{4-[6,6-Bis-(4-fluoro-phenyl)-hexanoylamino]-but-2-ynyl}-4-tert-butyl-benzamide | 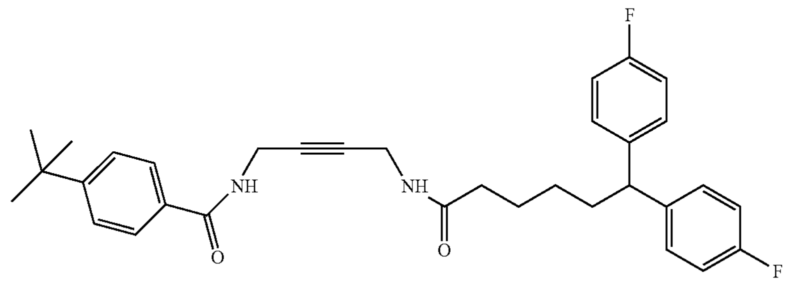 |
| P25 | N-{4-[6,6-Bis-(4-fluoro-phenyl)-hexanoylamino]-but-2-ynyl}-4-isopropyl-benzamide | 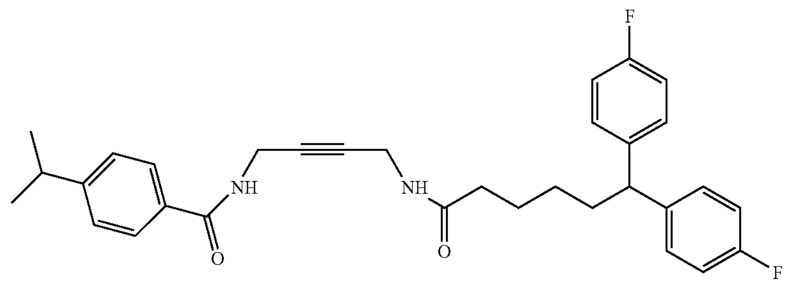 |
| P26 | N-{4-[6,6-Bis-(4-fluoro-phenyl)-hexanoylamino]-but-2-ynyl}-4-methyl-benzamide | 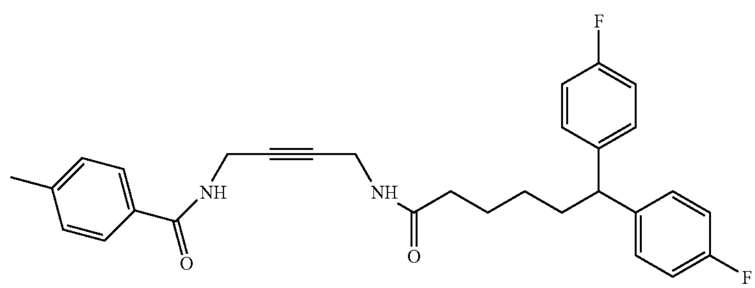 |
| P27 | N-{4-[6,6-Bis-(4-fluoro-phenyl)-hexanoylamino]-but-2-ynyl}-4-methoxy-benzamide | 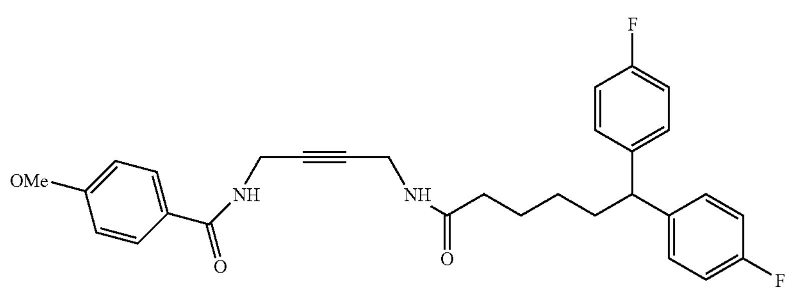 |
| P28 | N-{4-[6,6-Bis-(4-fluoro-phenyl)-hexanoylamino]-but-2-ynyl}-4-chloro-benzamide | 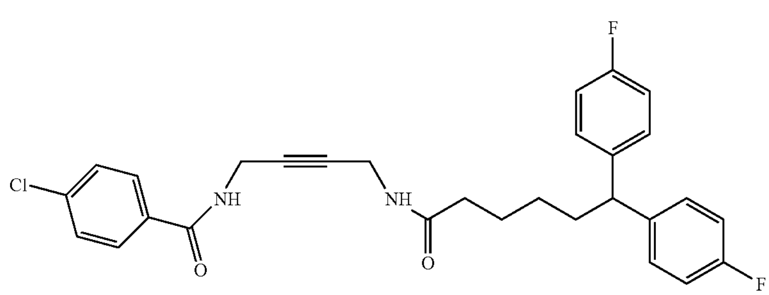 |

-continued
| Compound No. | Chemical name | Structure |
|---|---|---|
| P29 | N-{4-[6,6-Bis-(4-fluoro-phenyl)-hexanoylamino]-but-2-ynyl}-4-fluoro-benzamide | 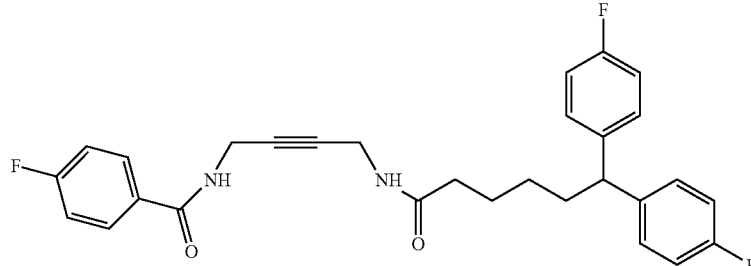 |
| P30 | N-[4-(Bis-pyridin-4-ylmethyl-amino)-but-2-ynyl]-3,3-diphenyl-propionamide | 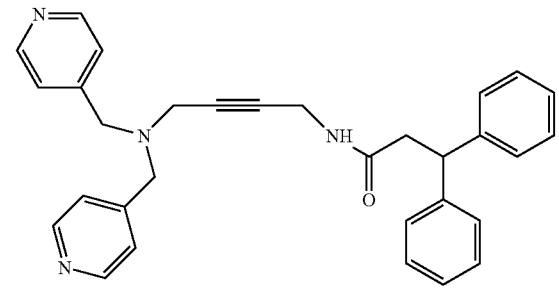 |
| P31 | N-[4-(Bis-pyridin-3-ylmethyl-amino)-but-2-ynyl]-3,3-diphenyl-propionamide | 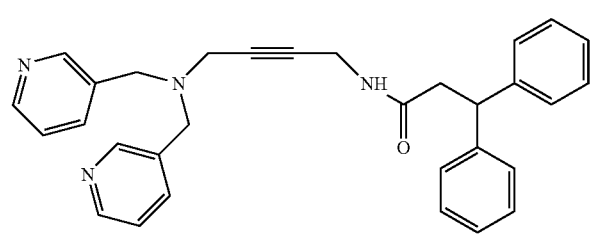 |
| P32 | N-[4-(Bis-pyridin-2-ylmethyl-amino)-but-2-ynyl]-3,3-diphenyl-propionamide | 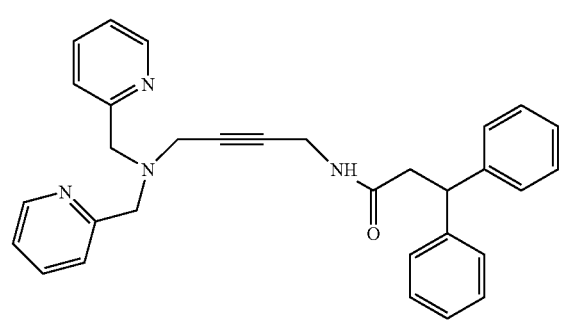 |
| P33 | 3,3-Diphenyl-N-{4-[(pyridin-2-ylmethyl)-amino]-but-2-ynyl}-propionamide | 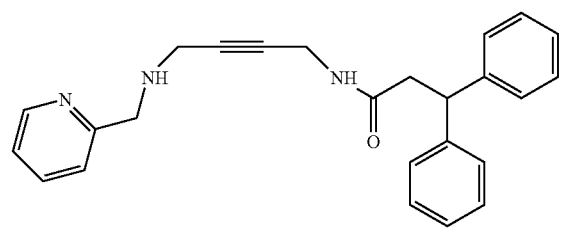 |

-continued

| Compound No. | Chemical name | Structure |
|---|---|---|
| P34 | N-{4-[6,6-Bis-(4-fluoro-phenyl)-hexanoylamino]-butyl}-4-tert-butyl-benzamide | 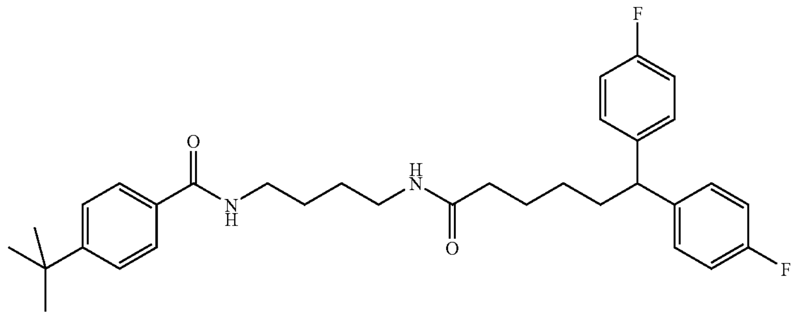 |
| P35 | N-{4-[6,6-Bis-(4-fluoro-phenyl)-hexanoylamino]-butyl}-3,5-bis-trifluoromethyl-benzamide | 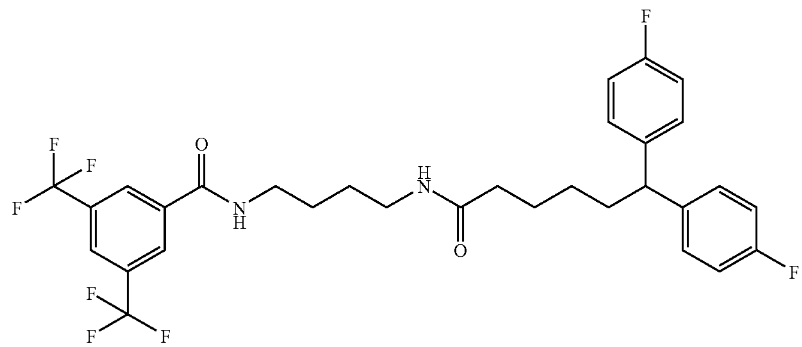 |
| P36 | 6,6-Bis-(4-fluoro-phenyl)-hexanoic acid{4-[2-(4-chloro-phenoxy)-acetylamino]-butyl}-amide | 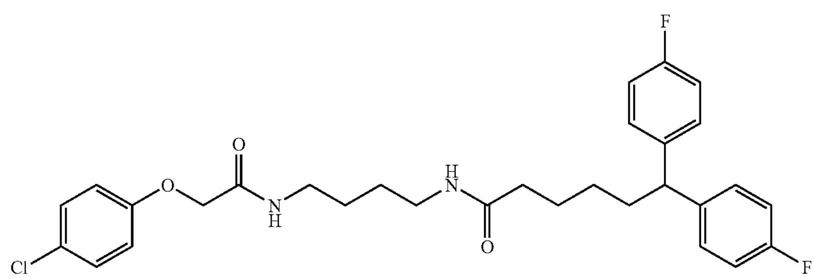 |
| P37 | N-{4-[6,6-Bis-(4-fluoro-phenyl)-hexanoylamino]-butyl}-4-isopropyl-benzamide | 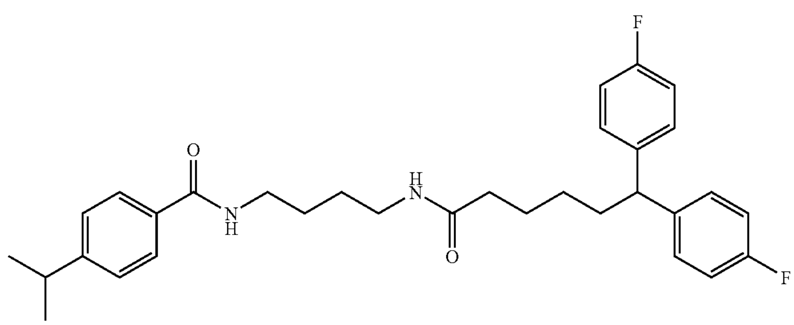 |

EXAMPLE 5

N-type Channel Blocking Activities of Various Invention Compounds

A. Transformation of HEK Cells:

N-type calcium channel blocking activity was assayed in human embryonic kidney cells, HEK 293, stably transfected with the rat brain N-type calcium channel subunits ($\alpha_{1B}$+$\alpha_2\delta$+$\beta_{1b}$ cDNA subunits). Alternatively, N-type calcium channels ($\alpha_{1B}$+$\alpha_2\delta$+$\beta_{1b}$ cDNA subunits), L-type channels ($\alpha_{1C}$+$\alpha_2\delta$+$\beta_{1b}$ cDNA subunits) and P/Q-type channels ($\alpha_{1A}$+$\alpha_2\delta$+$\beta_{1b}$ cDNA subunits) were transiently expressed in HEK 293 cells. Briefly, cells were cultured in Dulbecco's modified eagle medium (DMEM) supplemented with 10% fetal bovine serum, 200 U/ml penicillin and 0.2 mg/ml streptomycin at 37° C. with 5% $CO_2$. At 85% confluency cells were split with 0.25% trypsin/1 mM EDTA and plated at 10% confluency on glass coverslips. At 12 hours the medium was replaced and the cells transiently transfected using a standard calcium phosphate protocol and the appropriate calcium channel cDNA's. Fresh DMEM was supplied and the cells transferred to 28° C./5% $CO_2$. Cells were incubated for 1 to 2 days prior to whole cell recording.

B. Measurement of Inhibition

Whole cell patch clamp experiments were performed using an Axopatch 200B amplifier (Axon Instruments, Burlingame, Calif.) linked to a personal computer equipped with pCLAMP software. The external and internal recording solutions contained, respectively, 5 mM $BaCl_2$, 10 mM $MgCl_2$, 10 mM HEPES, 40 mM TEACl, 10 mM glucose, 87.5 mM CsCl (pH 7.2) and 108 mM CsMS, 4 mM $MgCl_2$, 9 mM EGTA, 9 mM HEPES (pH 7.2). Currents were typically elicited from a holding potential of −80 mV to +10 mV using Clampex software (Axon Instruments). Typically, currents were first elicited with low frequency stimulation (0.067 Hz) and allowed to stabilize prior to application of the compounds. The compounds were then applied during the low frequency pulse trains for two to three minutes to assess tonic block, and subsequently the pulse frequency was increased to 0.2 Hz to assess frequency dependent block. Data were analyzed using Clampfit (Axon Instruments) and SigmaPlot 4.0 (Jandel Scientific).

Specific data obtained for N-type channels are shown in Table 2 below.

TABLE 2

N-type Calcium Channel Block

| Compound | $IC_{50}$ @ 0.067 Hz (μM) | $IC_{50}$ @ 0.2 Hz (μM) |
|---|---|---|
| P1 | 0.23 | 0.19 |
| P2 | 0.43 | 0.31 |
| P3 | 0.47 | 0.27 |
| P4 | 0.086 | 0.059 |
| P5 | 0.074 | 0.046 |
| P6 | 0.058 | 0.027 |
| P7 | 0.097 | 0.054 |
| P10 | 0.182 | 0.112 |
| P11 | 0.331 | 0.196 |
| P12 | 0.22 | 0.146 |
| P13 | 0.79 | 0.54 |
| P14 | 0.51 | 0.38 |
| P15 | 0.019 | 0.127 |
| P16 | 0.052 | 0.015 |
| P17 | 0.598 | 0.266 |
| P18 | 0.809 | 0.305 |
| P19 | 0.182 | 0.132 |
| P20 | 0.188 | 0.134 |
| P21 | 0.514 | 0.278 |
| P22 | 0.237 | 0.139 |
| P23 | | |
| P24 | | |
| P25 | 0.77 | 0.76 |
| P26 | 0.144 | 0.04 |
| P27 | | |
| P28 | 0.36 | 0.36 |
| P29 | 0.29 | 0.29 |
| P30 | 0.34 | 0.33 |
| P31 | 0.42 | 0.42 |
| P32 | 2.2 | 0.568 |
| P33 | | |
| P34 | 0.291 | 0.165 |
| P35 | | |
| P36 | 0.039 | 0.01 |
| P37 | 0.31 | 0.3 |

EXAMPLE 6

T-Type Channel Blocking Activities of Various Invention Compounds

Standard patch-clamp techniques were employed to identify blockers of T-type currents. Briefly, previously described HEK cell lines stably expressing human $α_{1G}$ T-type channels were used for all the recordings (passage #: 4-20, 37° C., 5% $CO_2$). To obtain T-type currents, plastic dishes containing semi-confluent cells were positioned on the stage of a ZEISS AXIOVERT S100 microscope after replacing the culture medium with external solution (see below). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (see below for internal solution).

TABLE 3

External Solution 500 ml - pH 7.4, 265.5 mOsm

| Salt | Final mM | Stock M | Final ml |
|---|---|---|---|
| CsCl | 132 | 1 | 66 |
| $CaCl_2$ | 2 | 1 | 1 |
| $MgCl_2$ | 1 | 1 | 0.5 |
| HEPES | 10 | 0.5 | 10 |
| glucose | 10 | — | 0.9 grams |

TABLE 4

Internal Solution 50 ml - pH 7.3 with CsOH, 270 mOsm

| Salt | Final mM | Stock M | Final ml |
|---|---|---|---|
| Cs-Methanesulfonate | 108 | — | 1.231 gr/50 ml |
| MgCl2 | 2 | 1 | 0.1 |
| HEPES | 10 | 0.5 | 1 |
| EGTA-Cs | 11 | 0.25 | 2.2 |
| ATP | 2 | 0.2 | 0.025 |
| | | | (1 aliquot/2.5 ml) |

T-type currents were reliably obtained by using two voltage protocols:

(1) "non-inactivating", and (2) "inactivation"

In the non-inactivating protocol, the holding potential is set at −110 mV and with a pre-pulse at −100 mV for 1 second prior to the test pulse at −40 mV for 50 ms. In the inactivation protocol, the pre-pulse is at approximately −85 mV for 1 second, which inactivates about 15% of the T-type channels.

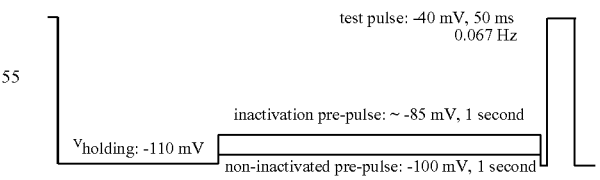

Test compounds were dissolved in external solution, 0.1-0.01% DMSO. After ~10 min rest, they were applied by gravity close to the cell using a WPI microfil tubing. The "non-inactivated" pre-pulse was used to examine the resting block of a compound. The "inactivated" protocol was employed to study voltage-dependent block. However, the initial data shown below were mainly obtained using the non-inactivated protocol only. IC$_{50}$ values are shown for various compounds of the invention in Table 5.

TABLE 5

T-type Calcium Channel Block

| Compound | IC$_{50}$ @ −100 mV (μM) | IC$_{50}$ @ −80 mV (μM) |
|---|---|---|
| P1 | | |
| P2 | | |
| P3 | | |
| P4 | 0.038 | 0.012 |
| P5 | 0.027 | 0.007 |
| P6 | 0.128 | 0.067 |
| P7 | 0.196 | 0.056 |
| P10 | 0.020 | 0.006 |
| P11 | 0.155 | 0.051 |
| P12 | 0.112 | 0.034 |
| P13 | | |
| P14 | | |
| P15 | 0.054 | 0.021 |
| P16 | 0.026 | 0.007 |
| P17 | 0.007 | 0.003 |
| P18 | 0.149 | 0.039 |
| P19 | 0.022 | 0.009 |
| P20 | 0.126 | 0.043 |
| P21 | 0.423 | 0.163 |
| P22 | 0.358 | 0.078 |
| P23 | | |
| P24 | | |
| P25 | 1.000 | 0.424 |
| P26 | 0.336 | 0.202 |
| P27 | | |
| P28 | 0.072 | 0.029 |
| P29 | 0.696 | 0.101 |
| P30 | 0.082 | 0.021 |
| P31 | 0.094 | 0.027 |
| P32 | 1.800 | 1.100 |
| P33 | | |
| P34 | 0.177 | 0.141 |
| P35 | | |
| P36 | 0.063 | 0.029 |
| P37 | 0.031 | 0.008 |

EXAMPLE 7

Effects of the Invention Compounds on Pre-contracted Rings Obtained from Rat Mesenteric Artery and Portal Vein Sprague-Dawley rats (350-400 g, Charles River Canada) were anaesthetized with sodium pentobarbital (60 mg/kg). The mesenteric arteries were removed and suspended in a tissue bath filled with Krebs-Henseleit solution aerated with 95% O$_2$ and 5% CO$_2$ at 37° C. The tissues were equilibrated for one hour prior to the construction of a concentration-response curve to phenylephrine (PE). Following recovery of the response to PE, a second curve to PE was constructed at 5 min after the addition of a calcium channel blocker (n=2-8, each from a separate rat) or the vehicle (50 μl of equimolar DMSO). After recovery, a third and fourth curve to PE were constructed after addition of a higher concentration of blocker or vehicle. The protocol was repeated using portal veins (n=4, each from a separate rat).

TABLE 6

Actions of Invention Compounds at 10$^{-5}$ M, on Rings from Rat Mesenteric Artery and Portal Vein Maximally Pre-Contracted with PE at 10$^{-4}$ M

| Compound # | Mesenteric artery Max % relax | Portal vein Max % relax | BP SHR at 4 hrs % reduction |
|---|---|---|---|
| P4 | 8 n = 2 | — | — |
| P5 | 10 n = 2 | — | — |
| P6 | 35 n = 4 | 28 n = 4 | — |
| P10 | 35 n = 4 | 38 n = 4 | — |
| P15 | 9 n = 2 | — | — |
| P23 | 0 n = 2 | — | — |
| P24 | 0 n = 2 | — | — |
| P26 | 40 n = 6 | 34 n = 4 | — |
| P27 | 41 n = 4 | 51 n = 4 | — |
| P28 | 61 n = 5 | 25 n = 2 | 13 n = 4 |
| P29 | 63 n = 6 | 51 n = 4 | — |
| P32 | 50 n = 4 | 49 n = 4 | — |
| P37 | 42 n = 4 | 51 n = 2 | — |

The invention claimed is:

1. A compound of the formula $$(Ar^1—X^1)_n—NR^1—X^3—NR^2—X^2—CR^3(Ar^2)_2 \quad (1)$$
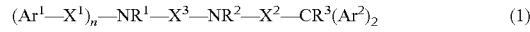

or a salt and conjugates thereof, wherein
each Ar$^1$ is independently a cyclic moiety which is aromatic and carbocyclic;
X$^1$ is a linker comprising a chain of 1-5 members;
n is 1 or 2;
R$^1$ is absent when n is 2 and when n is 1, R$^1$ is H, alkyl (1-8C), alkenyl (2-8C) or alkynyl (2-8C);
X$^3$ is alkylene, alkenylene or alkynylene (2-8C);
R$^2$ is H,
X$^2$ is alkylene (2-6C) substituted with ═O at the carbon adjacent the nitrogen to which X$^2$ is bound;
R$^3$ is H, OH or alkyl (1-4C);
each Ar$^2$ independently comprises a phenyl ring
wherein each Ar$^1$ and Ar$^2$ in formula (1) may be unsubstituted or substituted by one or more substituents selected from the group consisting of alkyl (1-8C), alkenyl (2-8C), alkynyl (2-8C), aryl, alkylaryl, halo, CHF$_2$, CF$_3$, OCF$_3$, OCHF$_2$, CN, NO$_2$, NR$_2$, OR, SR, COR, COOR, CONR$_2$, SOR, SO$_2$R, SO$_3$R, SONR$_2$, SO$_2$NR$_2$, SO$_3$NR$_2$, NROCR, OOCR, NRSOR, NRSO$_2$R, and NRSO$_3$R, wherein R is H, alkyl (1-8C), alkenyl (2-8C), alkynyl (2-8C), aryl, or alkylaryl or heteroforms of any of the foregoing, each of which may optionally be substituted, and wherein two R on the same N may form a 5-7 membered ring, and wherein two substituents on adjacent atoms may form a 5-7 membered ring; and
wherein the chain comprised in X$^1$ and X$^2$ may be substituted by ═O, alkyl (1-8C), alkenyl (2-8C), alkynyl (2-8C), halo, CHF$_2$, CF$_3$, OCF$_3$, OCHF$_2$, CN, NO$_2$, NR$_2$, OR, SR, COR, COOR, CONR$_2$, SOR, SO$_2$R, SO$_3$R, SONR$_2$, SO$_2$NR$_2$, SO$_3$NR$_2$, NROCR, OOCR, NRSOR, NRSO$_2$R, and/or NRSO$_3$R, wherein R is H or alkyl (1-8C), alkenyl (2-8C), alkynyl (2-8C), aryl, or alkylaryl or heteroforms of any of the foregoing, each of which may optionally be substituted wherein two R on the same N may form a 5-7 membered ring, and wherein two substituents on adjacent atoms may form a 5-7 membered ring.

2. The compound of claim 1, wherein each Ar$^1$ is phenyl.

3. The compound of claim 1, wherein n is 2 and both (Ar$^1$—X$^1$) groups are identical.

4. The compound of claim 1, wherein each X$^1$ is independently alkylene, alkenylene, alkynylene or a heteroatom-containing form thereof, optionally substituted with =O at the position adjacent the nitrogen to which $X^1$ is bound.

5. The compound of claim 4, wherein $X^1$ is unsubstituted alkylene.

6. The compound of claim 4, wherein $X^1$ is alkylene substituted with =O at the position adjacent the nitrogen to which $X^1$ is bound.

7. The compound of claim 1, wherein $X^1$ is C=O.

8. The compound of claim 1, wherein each $R^1$ is H or lower alkyl (1-4C).

9. The compound of claim 1, wherein $X^3$ is cis or trans but-2-enylene, cis or trans pent-2-enylene, but-2-ynylene, pent-2-ynylene, or is $(CH_2)_m$ wherein m is 2-5.

10. The compound of claim 1, wherein $R^3$ is H.

11. The compound of claim 1, wherein $Ar^2$ are identical.

12. The compound of claim 1, wherein both $Ar^2$ are substituted by halo.

13. The compound of claim 1 selected from the group consisting of
N-{(Z)-4-[6,6-Bis-(4-fluoro-phenyl)-hexanoylamino]-but-2-enyl}-3,4,5-trimethoxy-benzamide
N-{(Z)-4-[6,6-Bis-(4-fluoro-phenyl)-hexanoylamino]-but-2-enyl}-3,5-di-tert-butyl-4-methoxy-benzamide
N-{(Z)-4-[6,6-Bis-(4-fluoro-phenyl)-hexanoylamino]-but-2-enyl}-3,5-di-tert-butyl-4-hydroxy-benzamide
N-{(Z)-4-[6,6-Bis-(4-fluoro-phenyl)-hexanoylamino]-but-2-enyl}-4-tert-butyl-benzamide
N-{(Z)-4-[6,6-Bis-(4-fluoro-phenyl)-hexanoylamino]-but-2-enyl}-3,5-bis-trifluoromethyl-benzamide
6,6-Bis-(4-fluoro-phenyl)-hexanoic acid{(Z)-4-[2-(4-chloro-phenoxy)-acetylamino]-but-2-enyl}-amide
N-{(Z)-4-[6,6-Bis-(4-fluoro-phenyl)-hexanoylamino]-but-2-enyl}-4-isopropyl-benzamide
N-{(Z)-4-[6,6-Bis-(4-fluoro-phenyl)-hexanoylamino]-but-2-enyl}-4-chloro-benzamide
N-{(Z)-4-[6,6-Bis-(4-fluoro-phenyl)-hexanoylamino]-but-2-enyl}-4-methyl-benzamide
N-{(Z)-4-[6,6-Bis-(4-fluoro-phenyl)-hexanoylamino]-but-2-enyl}-4-fluoro-benzamide
N-{(E)-4-[6,6-Bis-(4-fluoro-phenyl)-hexanoylamino]-but-2-enyl}-3,4,5-trimethoxy-benzamide
N-{(E)-4-[6,6-Bis-(4-fluoro-phenyl)-hexanoylamino]-but-2-enyl}-3,5-di-tert-butyl-4-methoxy-benzamide
N-{(E)-4-[6,6-Bis-(4-fluoro-phenyl)-hexanoylamino]-but-2-enyl}-3,5-di-tert-butyl-4-hydroxy-benzamide
N-{(E)-4-[6,6-Bis-(4-fluoro-phenyl)-hexanoylamino]-but-2-enyl}-4-tert-butyl-benzamide
N-{(E)-4-[6,6-Bis-(4-fluoro-phenyl)-hexanoylamino]-but-2-enyl}-3,5-bis-trifluoromethyl-benzamide
6,6-Bis-(4-fluoro-phenyl)-hexanoic acid{(E)-4-[2-(4-chloro-phenoxy)-acetylamino]-but-2-enyl}-amide
N-{(E)-4-[6,6-Bis-(4-fluoro-phenyl)-hexanoylamino]-but-2-enyl}-4-isopropyl-benzamide
N-{(E)-4-[6,6-Bis-(4-fluoro-phenyl)-hexanoylamino]-but-2-enyl}-4-chloro-benzamide
N-{(E)-4-[6,6-Bis-(4-fluoro-phenyl)-hexanoylamino]-but-2-enyl}-4-methyl-benzamide
N-{(E)-4-[6,6-Bis-(4-fluoro-phenyl)-hexanoylamino]-but-2-enyl}-4-fluoro-benzamide
N-{4-[6,6-Bis-(4-fluoro-phenyl)-hexanoylamino]-but-2-ynyl}-3,4,5-trimethoxy-benzamide
N-{4-[6,6-Bis-(4-fluoro-phenyl)-hexanoylamino]-but-2-ynyl}-3,5-di-tert-butyl-4-methoxy-benzamide
N-{4-[6,6-Bis-(4-fluoro-phenyl)-hexanoylamino]-but-2-ynyl}-4-tert-butyl-benzamide
N-{4-[6,6-Bis-(4-fluoro-phenyl)-hexanoylamino]-but-2-ynyl}-4-isopropyl-benzamide
N-{4-[6,6-Bis-(4-fluoro-phenyl)-hexanoylamino]-but-2-ynyl}-4-methyl-benzamide
N-{4-[6,6-Bis-(4-fluoro-phenyl)-hexanoylamino]-but-2-ynyl}-4-methoxy-benzamide
N-{4-[6,6-Bis-(4-fluoro-phenyl)-hexanoylamino]-but-2-ynyl}-4-chloro-benzamide
N-{4-[6,6-Bis-(4-fluoro-phenyl)-hexanoylamino]-but-2-ynyl}-4-fluoro-benzamide
N-{4-[6,6-Bis-(4-fluoro-phenyl)-hexanoylamino]-butyl}-4-tert-butyl-benzamide
N-{4-[6,6-Bis-(4-fluoro-phenyl)-hexanoylamino]-butyl}-3,5-bis-trifluoromethyl-benzamide
6,6-Bis-(4-fluoro-phenyl)-hexanoic acid{4-[2-(4-chloro-phenoxy)-acetylamino]-butyl}-amide and
N-{4-[6,6-Bis-(4-fluoro-phenyl)-hexanoylamino]-butyl}-4-isopropyl-benzamide.

14. A pharmaceutical composition which comprises the compound of claim 1 in admixture with a pharmaceutically acceptable excipient.

15. The pharmaceutical composition of claim 14, wherein $X^1$ is alkylene substituted with =O at the position adjacent the nitrogen to which $X^1$ is bound.

16. The pharmaceutical composition of claim 14, wherein $X^1$ is C=O.

17. The pharmaceutical composition of claim 14, wherein $X^3$ is cis or trans but-2-enylene, cis or trans pent-2-enylene, but-2-ynylene, pent-2-ynylene, or is $(CH_2)_m$ wherein m is 2-5.

18. The pharmaceutical composition of claim 14, wherein the compound is selected from the group consisting of:
N-{(Z)-4-[6,6-Bis-(4-fluoro-phenyl)-hexanoylamino]-but-2-enyl}-3,4,5-trimethoxy-benzamide
N-{(Z)-4-[6,6-Bis-(4-fluoro-phenyl)-hexanoylamino]-but-2-enyl}-3,5-di-tert-butyl-4-methoxy-benzamide
N-{(Z)-4-[6,6-Bis-(4-fluoro-phenyl)-hexanoylamino]-but-2-enyl}-3,5-di-tert-butyl-4-hydroxy-benzamide
N-{(Z)-4-[6,6-Bis-(4-fluoro-phenyl)-hexanoylamino]-but-2-enyl}-4-tert-butyl-benzamide
N-{(Z)-4-[6,6-Bis-(4-fluoro-phenyl)-hexanoylamino]-but-2-enyl}-3,5-bis-trifluoromethyl-benzamide
6,6-Bis-(4-fluoro-phenyl)-hexanoic acid{(Z)-4-[2-(4-chloro-phenoxy)-acetylamino]-but-2-enyl}-amide
N-{(Z)-4-[6,6-Bis-(4-fluoro-phenyl)-hexanoylamino]-but-2-enyl}-4-isopropyl-benzamide
N-{(Z)-4-[6,6-Bis-(4-fluoro-phenyl)-hexanoylamino]-but-2-enyl}-4-chloro-benzamide
N-{(Z)-4-[6,6-Bis-(4-fluoro-phenyl)-hexanoylamino]-but-2-enyl}-4-methyl-benzamide
N-{(Z)-4-[6,6-Bis-(4-fluoro-phenyl)-hexanoylamino]-but-2-enyl}4-fluoro-benzamide
N-{(E)-4-[6,6-Bis-(4-fluoro-phenyl)-hexanoylamino]-but-2-enyl}-3,4,5-trimethoxy-benzamide
N-{(E)-4-[6,6-Bis-(4-fluoro-phenyl)-hexanoylamino]-but-2-enyl}-3,5-di-tert-butyl-4-methoxy-benzamide
N-{(E)-4-[6,6-Bis-(4-fluoro-phenyl)-hexanoylamino]-but-2-enyl}-3,5-di-tert-butyl-4-hydroxy-benzamide
N-{(E)-4-[6,6-Bis-(4-fluoro-phenyl)-hexanoylamino]-but-2-enyl}-4-tert-butyl-benzamide
N-{(E)-4-[6,6-Bis-(4-fluoro-phenyl)-hexanoylamino]-but-2-enyl}-3,5-bis-trifluoromethyl-benzamide
6,6-Bis-(4-fluoro-phenyl)-hexanoic acid{(E)-4-[2-(4-chloro-phenoxy)-acetylamino]-but-2-enyl}-amide
N-{(E)-4-[6,6-Bis-(4-fluoro-phenyl)-hexanoylamino]-but-2-enyl}-4-isopropyl-benzamide
N-{(E)-4-[6,6-Bis-(4-fluoro-phenyl)-hexanoylamino]-but-2-enyl}-4-chloro-benzamide N-{(E)-4-[6,6-Bis-(4-fluoro-phenyl)-hexanoylamino]-but-2-enyl}-4-methyl-benzamide N-{(E)-4-[6,6-Bis-(4-fluoro-phenyl)-hexanoylamino]-but-2-enyl}-4-fluoro-benzamide N-{4-[6,6-Bis-(4-fluoro-phenyl)-hexanoylamino]-but-2-ynyl}-3,4,5-trimethoxy-benzamide N-{4-[6,6-Bis-(4-fluoro-phenyl)-hexanoylamino]-but-2-ynyl}-3,5-di-tert-butyl-4-methoxy-benzamide N-{4-[6,6-Bis-(4-fluoro-phenyl)-hexanoylamino]-but-2-ynyl}-4-tert-butyl-benzamide N-{4-[6,6-Bis-(4-fluoro-phenyl)-hexanoylamino]-but-2-ynyl}-4-isopropyl-benzamide N-{4-[6,6-Bis-(4-fluoro-phenyl)-hexanoylamino]-but-2-ynyl}-4-methyl-benzamide N-{4-[6,6-Bis-(4-fluoro-phenyl)-hexanoylamino]-but-2-ynyl}-4-methoxy-benzamide N-{4-[6,6-Bis-(4-fluoro-phenyl)-hexanoylamino]-but-2-ynyl}-4-chloro-benzamide N-{4-[6,6-Bis-(4-fluoro-phenyl)-hexanoylamino]-but-2-ynyl}-4-fluoro-benzamide N-{4-[6,6-Bis-(4-fluoro-phenyl)-hexanoylamino]-butyl}-4-tert-butyl-benzamide N-{4-[6,6-Bis-(4-fluoro-phenyl)-hexanoylamino]-butyl}-3,5-bis-trifluoromethyl-benzamide 6,6-Bis-(4-fluoro-phenyl)-hexanoic acid{4-[2-(4-chloro-phenoxy)-acetylamino]-butyl}-amide and N-{4-[6,6-Bis-(4-fluoro-phenyl)-hexanoylamino]-butyl}-4-isopropyl-benzamide.

\* \* \* \* \*